(12) United States Patent
Albu et al.

(10) Patent No.: US 8,508,222 B2
(45) Date of Patent: Aug. 13, 2013

(54) NUCLEAR MAGNETIC RESONANCE SPECTROSCOPY USING LIGHT WITH ORBITAL ANGULAR MOMENTUM

(75) Inventors: Lucian Remus Albu, Forest Hills, NY (US); Daniel R. Elgort, New York, NY (US); Satyen Mukherjee, Yorktown Heights, NY (US)

(73) Assignee: Koninklijke Philips N.V., Eindhoven (NL)

( * ) Notice: Subject to any disclaimer, the term of this patent is extended or adjusted under 35 U.S.C. 154(b) by 432 days.

(21) Appl. No.: 12/812,900

(22) PCT Filed: Jan. 15, 2009

(86) PCT No.: PCT/IB2009/050145
§ 371 (c)(1),
(2), (4) Date: Jul. 14, 2010

(87) PCT Pub. No.: WO2009/090610
PCT Pub. Date: Jul. 23, 2009

(65) Prior Publication Data
US 2010/0327866 A1    Dec. 30, 2010

Related U.S. Application Data

(60) Provisional application No. 61/022,984, filed on Jan. 23, 2008.

(51) Int. Cl.
*G01R 33/46*    (2006.01)
(52) U.S. Cl.
USPC .......................................... 324/304; 250/251

(58) Field of Classification Search
USPC ........................................................ 324/304
See application file for complete search history.

(56) References Cited

U.S. PATENT DOCUMENTS

| 4,654,593 | A * | 3/1987 | Ackerman | 324/307 |
| 6,180,940 | B1 * | 1/2001 | Galstian | 250/251 |
| 6,845,262 | B2 | 1/2005 | Albert | |
| 2007/0080684 | A1 | 4/2007 | Appelt | |

FOREIGN PATENT DOCUMENTS

| WO | 03023356 A2 | 3/2003 |
| WO | 2006003065 A1 | 1/2006 |

OTHER PUBLICATIONS

Ebrahimi, Behzad et al "The Effect of Noise and Depolarization on Hyperpolarized Tracers Perfusion Assessment" IEEE Int. Sym. Biomedical Imaging, pp. 137-140, Apr. 2007.
Elgort, D.R. et al "Direct Optical Hyperpolarization of Liquids" Proceedngs of the International Society for Magnetic Resonance in Medicine, May 3, 2008, pp. 3200.

(Continued)

*Primary Examiner* — Patrick Assouad
*Assistant Examiner* — Rishi Patel

(57) ABSTRACT

A device capable of producing a high resolution chemical analysis of a sample, such as fluid, is based upon nuclear magnetic resonance (NMR) spectroscopy. The nuclear magnetic polarizations of the sample are generated by sequentially illuminating the sample with a focused beam of light carrying angular orbital angular momentum (OAM) and possibly momentum (spin). Unlike in a typical NMR used for magnetic nuclear resonance imaging (MRI) or spectroscopy, the present device does not make use of a strong magnet.

15 Claims, 7 Drawing Sheets

(56) References Cited

OTHER PUBLICATIONS

Godbout, Nicolas et al "Photons with an Orbital Angular Momentum Generated in an Optical Fiber" Quantum Electronics and Laser Science Conference, vol. 2, May 22, 2005, pp. 720-722.

Leach, Jonathan et al "Observation of Chromatic Effects near a White-Light Vortex", New Journal of Physics, vol. 5, No. 1, Nov. 1, 2003, pp. 154,1-154.7.

Wu, Xizeng "Optical Pumping and Hyperpolarized Spin Relaxation" Proc. SPIE, Third International Conf> on Photonics and Imaging in Biology and Medicine, vol. 5254, 2003, pp. 97-107.

Wu, Xizeng "Spin Relaxation for Laser-Pumped Hyperpolarized Spins" Proc. SPIE, vol. 3548, 1998, pp. 67-74.

Allen, L. et al "The Orbital Angular Momentum of Light and the Transformation ofLagueere-Gaussian Laser Modes" Physical Review A, vol. 45, No. 11, Jun. 1992, pp. 8185-8190.

* cited by examiner (R is hydrogen or methyl)

NUCLEAR MAGNETIC RESONANCE SPECTROSCOPY USING LIGHT WITH ORBITAL ANGULAR MOMENTUM

This application is a national stage application under 35 U.S.C. §371 of International Application No. PCT/IB2009/050145, filed on Jul. 14, 2010, which claims priority to U.S. Provisional Application No. 61/022,984, filed on Jan. 23, 2008.

FIELD OF THE INVENTION

The present invention relates to a sample analysis method based on nuclear magnetic resonance (NMR) spectroscopy. The invention also relates to a corresponding computer program product and device for carrying out the method.

BACKGROUND OF THE INVENTION

NMR is usually pursued in a setup based on a highly homogenous static magnetic field with spatial variation of less than 1 ppm, creating nuclear spin precession at a corresponding narrow frequency band of frequencies. However, this setup suffers from the need to employ strong and homogenous magnets, radio frequency (RF) and gradient coils that usually surround the examined sample, such as blood sample or tissue biopsy, and are a major factor in the relative complexity and the high cost of such systems.

NMR has found applications in magnetic nuclear resonance imaging (MRI) (as its sensitivity to the chemical characteristics of tissue components makes it the modality of choice for tissue characterization and differentiating soft tissues), fluid chemical analysis of small molecules and biomolecules (protein-ligand interactions, protein folding, protein structure validation, protein structure determination), solid state analysis (structural), dynamics of time-variable systems (functional MRI), etc.

A company called "TopSpin Medical" has recently revealed an intra venous magnetic nuclear resonance imaging (IVMRI) catheter with a static magnetic field of about 0.2 Tesla generated by strong permanent magnets located at the tip of a catheter. This company has developed a self contained "inside-out" miniature MRI probe in a tip of an intravascular catheter that allows for local high-resolution imaging of blood vessels without the need for external magnets or coils. This probe is shown in FIG. 1. The advantages of this technique range from the very practical aspect of a low-cost system, since no expensive external setup is required, accessibility to the patient during the procedure, compatibility with existing interventional tools and finally resolution and diffusion contrast capabilities that are unattainable by conventional clinical MRI, due to the strong local gradients created by the probe and its proximity to the examined tissue. This intravascular probe serves as a first example for a wide range of applications for this method, which in the near future may revolutionize the field of clinical MRI. The medical applications for this technology include for instance detection and staging of prostate cancer, imaging tumors in the colon, lung and breast and intravascular imaging of the peripheral vasculature.

Micro NMR coils are also known for a skilled man in the art. Developments of these "micro MRI" devices depend on the existence of high quality receiving coils. Microelectromechanical systems (MEMS) breakthroughs have made possible this new technology for the micro fabrication of Helmholtz micro coils for NMR spectroscopy. These Helmholtz micro coils demonstrate superior NMR performance in terms of spin excitation uniformity compared to planar micro coils. The improved spin excitation uniformity opens the way to advanced chemical analysis by using complex RF-pulse sequences. The fabricated Helmholtz coils have Q-factor greater than 20 due to electroplated coil turns and vias, which connect the lower and upper turns. For analyzing living cells, mechanical filters can be integrated for sample concentration and enhanced detection.

NMR requires orienting a part of the nuclei magneton (spins) population along a chosen spatial direction. When oriented, the population is in a polarized state. This is usually achieved with strong magnetic fields, which are not attenuated by diamagnetic materials (biological tissue, fluids etc.). The net polarization achieved using magnetic fields is usually on the order of 5 to 25 parts per million. The nuclei spins of a material can be locally oriented by radiating the sample with circularly polarized light. Methods using circularly polarized light are able to achieve high levels of polarization, up to 40%, under the right circumstances. Polarizations in this order of magnitude are considered hyperpolarized. Hyperpolarizability is obtained through the hyperfine spin-spin interaction electron-nucleus, the electron-photon spin exchange and the electronic-spin population saturation due to Fermi's exclusion principle applied to molecule's electrons.

Optical pumping is used to produce hyperpolarized gases. Hyperpolarized gases have found a steadily increasing range of applications in MRI and NMR. They can be considered as a new class of MR contrast agent or as a way of greatly enhancing the temporal resolution of the measurement of processes relevant to areas as diverse as materials science and biomedicine. The physics of producing hyperpolarization involves irradiating samples of Na with intense circularly polarized lasers of a wave length corresponding to one of the absorption bands for Na, followed by a "mechanical" polarization transfer to inert $^{129}$Xe. The last is used as contrast agents in MRI and polarization transfer for other nuclear species for low-field imaging.

The NMR effect can be observed and measured with optical methods. All Optical NMR hyperfine interactions allow for flip-flop spin scattering. This means that an electron can flip its spin by flipping simultaneously a nucleus into the other direction. This leads to a dynamic polarization of the nuclear spins. If the electron spin levels are saturated by a driving field, i.e. the population of the upper spin state is made equal to that of the lower state, such flip-flop processes try to reestablish thermal equilibrium, resulting in a nuclear spin polarization, which is described by a Boltzmann factor where the electron Zeeman splitting enters. Because the electron splitting is usually 1000 times larger than the nuclear splitting, the nuclei end up in an up to 1000 times enhanced polarization compared to their thermal equilibrium value—also known as an Overhauser effect.

Yet another application of light angular momentum with magnetons is a high sensitivity-high frequency magnetometer. This solves one of the challenges raised by observing NMR effects, which is being able to measure the transient response of the magnetic fields produced by spinning nuclei. A magnetometer has been demonstrated operating by detecting optical rotation due to the precession of an aligned ground state in the presence of a small oscillating magnetic field. The projected sensitivity is around 20 pG/pHz (RMS).

In 1992 Allen et al., "Optical angular momentum", ISBN 0 7503 0901 6, verified the existence of light endowed with orbital angular momentum (OAM). Theoretical understanding and experimental evidence lead to applications, where light with OAM interacts with matter: optical tweezers, high throughput optical communication channels, optical encryption technique, optical cooling (Bose-Einstein condensates), entanglement of photons with OAM, entanglement of molecule quantum numbers with interacting photons OAM.

The Micro NMR is an appealing chemical analysis device for being included in an ePill device or in an inexpensive non-invasive blood analysis apparatus. It shall consume low power, be confined within a small volume and shall not include any paramagnetic materials (FDA). "TopSpin Medical" micro NMR or other "fixed magnet based" NMR are not suitable for the purpose, since these include a permanent magnet, require long acquisition time and hence consume power. An ePill is a small electronic device that is swallowed by a patient for performing an analysis of internal organs of the patient.

Photon-electron spin interaction has been extensively observed and modeled and it is the basis of the optical pumping technology for hyperpolarizability of gases. Unfortunately, this technique is not capable for producing fluid hyperpolarizability, due to thermal molecular movement and interactions.

Photon OAM interactions with nuclei has been recently analyzed as a method of controlling the spin-spin interaction within nuclei. It uses energetic X rays, not desirable for "in-vivo" applications.

Furthermore, by applying a constant magnetic field to a sample containing N nuclei, at room temperature, one can calculate the maximum number of oriented nuclei (Boltzmann distribution), which is around $10^{-5}N$. In order to extract a significant magnetic signal from the sample, one has to implement high quality factor coils or enlarge the size of the sample. In both cases the volume occupied by the receiver shall increase, which makes the permanent magnet micro NMR difficult to integrate within an ePill.

Thus, the object of the present invention is to provide an improved method and apparatus for a sample analysis based on NMR spectroscopy.

SUMMARY OF THE INVENTION

According to a first aspect of the invention there is provided a method of analyzing a sample consisting of molecules, the analysis being based upon nuclear magnetic resonance spectroscopy, the method comprising the following steps:
  turning on a light source;
  introducing orbital angular momentum into the light;
  obtaining a focused light beam carrying orbital angular momentum;
  sequentially illuminating the sample with the focused light beam carrying orbital angular momentum for obtaining nuclear magnetic polarizability of the sample; and
  obtaining a free induction decay signal resulting from the illumination, the free induction decay signal carrying characteristics of the sample.

This provides clear advantages, namely for instance the obtained free induction decay (FID) signal is much stronger than the corresponding signal obtained by using traditional NMR spectroscopy methods. Thus, the sensitivity of the measurement technique is greatly improved. The obtained FID signal is also less noisy and better resolution can be achieved. As a consequence smaller samples can be analyzed.

According to a second aspect of the invention there is provided a computer program product comprising instructions for implementing the method according the first aspect of the invention when loaded and run on computer means of an analysis device.

According to a third aspect of the invention there is provided a device for analyzing a sample consisting of molecules, the analysis being based upon nuclear magnetic resonance spectroscopy, the device comprises:
  a light source;
  means for introducing orbital angular momentum into the light;
  a recipient for accommodating the sample;
  means for obtaining a focused light beam;
  means for sequentially illuminating the sample with the focused light beam carrying orbital angular momentum for obtaining nuclear magnetic polarizability of the sample; and
  means for detecting a free induction decay signal resulting from the illumination, the free induction decay signal carrying characteristics of the sample.

BRIEF DESCRIPTION OF THE DRAWINGS

Other features and advantages of the invention will become apparent from the following description of non-limiting exemplary embodiments, with reference to the appended drawings, in which.

DETAILED DESCRIPTION OF THE INVENTION

Figure 1:
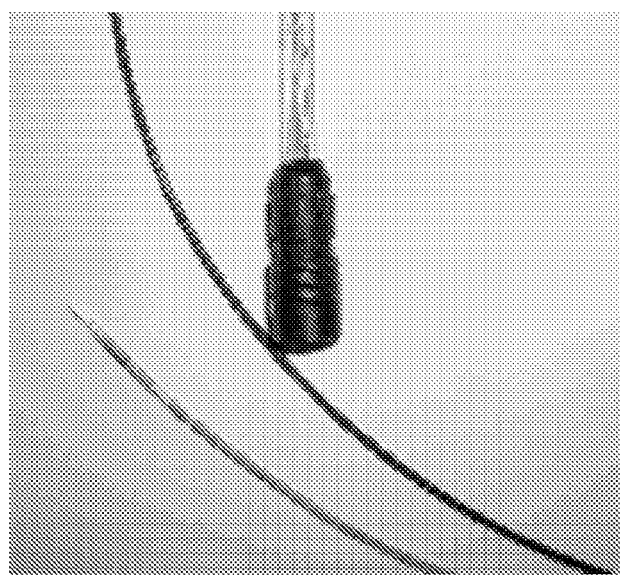
FIG. 1 shows a side view of a medical IVMRI probe.

In the following description some non-limiting exemplary embodiments of the invention for carrying out high resolution sample analysis will be described in more detail. Also the corresponding device will be described by use of exemplary block diagrams. It is to be noted that these are merely exemplary embodiments, but many variations are possible as becomes clear for a person skilled in the art by reading the following description.

The present invention is based on the fact that the OAM of absorbed photons is transferred to interacting molecules (angular momentum conservation) and as a consequence:

Electron state reaches a saturated spin state;

Angular momentum of the molecule (around centre of mass of the molecule) is increased and oriented along the propagation axis of incident light; and All magnetic magnetons precession movement associated with the molecules (including electrons and nucleons) are oriented along the propagation axis of incident light.

The above make possible to obtain hyperpolarizability of fluids by illuminating them with light carrying OAM and possibly spin, i.e. angular momentum, and implement an NMR device without a permanent magnet.

The quantum electrodynamics (QED) framework can be considered as a starting point for explaining the interaction of photons with OAM with matter. This has been applied for a hydrogenic model, and it has been found out that the OAM part of the incident light induces a rotation of the molecule, of a momentum equal to the light's momentum. This finding has been confirmed by stating from a more general Bessel model of light with OAM.

The spontaneous or stimulated emission of photons endowed with OAM is a phenomenon not yet understood, modeled or experimentally proven. Therefore, the generation of beams with OAM is accomplished through optical means of spatial phase change, interference and diffraction of Gaussian beams. Four methods (five if the two methods using cylindrical lenses are considered separate methods) are available as summarized in Table 1. In the table the power conversion efficiency is the ratio of the output power (beam with OAM) to the power of the input beam. Currently the highest OAM number obtained in a laboratory is as high as 10000 $\hbar L$ per photon. This is obtained by an elliptical Gaussian beam focused by a cylindrical lens.

TABLE 1

Methods for generating light with OAM.

| Input beam type | Mode Converter | OAM Variability | Power Conversion Efficiency | Notes |
|---|---|---|---|---|
| Hermite Gauss $TEM_{m,n}$ laser | Cylindrical lenses | NO | ~95% | Modified laser cavities and out of cavity cylindrical lenses to convert usual Hermite-Gauss $TEM_{m,n}$ laser modes into Laguerre-Gauss modes. The orbital angular momentum number l is given by l = m − n, so that high-order HG modes must be generated first. |
| Gauss $TEM_{00}$ laser | Cylindrical lenses posed at different angles | YES | ~95% | A set of cylindrical lenses posed at different angles in the path of a $TEM_{00}$ laser beam can produce a beam carrying orbital angular momentum (not eigenstate!). Beams carrying up to 10000h angular momentum per photon have been produced in this way. |
| Gauss $TEM_{00}$ laser | Phase plate | NO | 10 … 80% | Transparent plate micro machined such that the OAM phase singularities are mapped to the geometry of the plate. |
| Gauss $TEM_{00}$ laser | Hologram plate | NO | NA | Holographic plate that maps the OAM phase singularities to the holographic pattern on the plate. |
| Gauss $TEM_{00}$ laser modes | Computer generated hologram with space light modulator | YES | ~2% | Computer generated holograms that map the OAM phase singularities to holographic patterns. The holograms are applied to Space Light Modulator devices illuminated with lasers; may convert $TEM_{00}$ laser beams into $LG_{m,n}$ beams. |

Looking at the interaction of light endowed with OAM with molecules, it has been found that an exchange of orbital angular momentum in an electric dipole transition occurs only between the light and the centre of mass motion. In other words internal "electronic-type" motion does not participate in any exchange of orbital angular momentum in a dipole transition. It has been proved that the rotation/vibration of irradiated molecules increases with the value of the OAM. It has been further shown that photon OAM interacts with nucleons magnetons. Such transitions require photons with a high angular momentum and could be used for fine-tuning the processes of nuclear multipolarity transitions.

The NMR analysis technique lies on the following steps:
1. The sample nuclear magnetic momenta are oriented (precession movement) along a selected spatial direction. This is usually achieved with a strong magnetic field or—within more recent applications—with polarized light.
2. While in nuclear polarized state, one applies to the sample a sequence of magnetic fields, which triggers the free induction decay (FID) magnetic signal, representing the magnetic nuclei relaxation time from the magnetic sequence state to the polarized state.
3. The parameters in a nuclear magnetic resonance (NMR) FID signal contain information that is useful in biological and biomedical applications and research.

In contrast to the constant magnetic field NMR, the optical pump can achieve about 100% hyperpolarizability of the sample, i.e. about N nuclei will have the precession of their magnetic momentum oriented along the direction of propagation of pumping light. This makes possible the reduction of the sample and receiving coils, therefore the device could be integrated within an ePill. The signal to noise ratio is therefore improved by optical pumping as well as the power budget for the low noise amplifier (LNA) coil receiver.

The main concept of the present invention refers to a new method to orient the nuclei of a sample along a selected spatial direction using the interaction of light with OAM with molecules. The following sections focus on the theoretical explanation of this interaction and an experimental proof of the concept.

Following notations and symbols are used throughout the remaining description:
$\Re(z)$, $\Im(z)$, $\|z\|$ real part, imaginary part and modulus of a complex number z
$\vec{1}_x$, $\vec{1}_y$, $\vec{1}_z$, or $\hat{x}$, $\hat{y}$, $\hat{z}$ linear independent unit vectors for Cartesian coordinates system (Oxyz)
$\vec{1}_\rho$, $\vec{1}_\theta$, $\vec{1}_z$ or $\hat{\rho}$, $\hat{\theta}$, $\hat{z}$ linear independent unit vectors for Cartesian coordinates system (O$\rho\theta$z)
$\vec{v}_m$, $\vec{v}_{m,\theta}$, $\vec{v}_{m,\rho}$, $\vec{v}_{m,z}$, indexed m vector with its linear components in a cylindrical coordinates system:

$$\vec{v}_m = v_{m,\rho}\vec{1}_\rho + v_{m,\theta}\vec{1}_\theta + v_{m,z}\vec{1}_z$$

$\vec{r}$ x$\vec{1}_x$+y$\vec{1}_y$+z$\vec{1}_z$
c speed of light in vacuum
h ($\hbar$) Plank constant (h/2$\pi$)
$\vec{A}(\vec{r},t)$ electromagnetic potential vector
$\vec{A}_{pol}$ electromagnetic potential vector polarization
$\vec{E}(\vec{r},t)$ electric intensity vector field
$\vec{B}(\vec{r},t)$ magnetic intensity vector field
v Frequency
$\lambda$ wavelength (c/v)
$\omega$ angular frequency 2$\pi\lambda$
$\vec{k}$ wave vector 2$\pi/\lambda$ $\vec{1}_z$, k=$\|\vec{k}\|$=2$\pi/\lambda$
i complex unit $\sqrt{-1}$
$w_o$ beam radius (waist) at z=0
$z_R$ Raileight range, distance z at which beam section area doubles
w(z) beam radius $\sqrt{1+(z/z_R)^2}$
$L_n^k(x)$ $n^{th}$ order generalized Laguerre polynominal with parameter k evaluated at x, $$L_n^k(x) = \sum_{m=0}^{n} (-1)^m \frac{(n+k)!}{(n-m)!(k+m)!m!} x^m \cdot \forall k \in N,$$

$$\forall x \in R, L_0^k(x) \equiv 1$$

$\vec{v}_{l,p}$ vector associated to a Laguerre-Gauss electromagnetic wave of order l and parameter p.

$$\mu_n = \frac{e_n \hbar}{2m_n c}$$

Bohr magneton for a particle with charge $m_n$
Electromagnetic Equations for Laguerre-Gauss Beams
The classic electromagnetic wave equation for the potential vector $\vec{A}(\vec{r},t)$ (derived from Maxwell's equations) is:

$$\nabla^2 \vec{A}(\vec{r},t) = \frac{1}{c^2}\frac{\partial^2 \vec{A}(\vec{r},t)}{\partial t^2} = 0 \quad (1:1)$$

with $\nabla \cdot \vec{A}=0$. Assuming a null charge distribution in space $\Phi(\vec{r},t)=0$, the corresponding electromagnetic field strengths are:

$$\vec{E}(\vec{r},t) = -\nabla\phi - \frac{\partial}{\partial t}\vec{A}(\vec{r},t) = -\frac{\partial}{\partial t}\vec{A}(\vec{r},t) \quad (1:2)$$

$$\vec{B}(\vec{r},t) = \nabla \times \vec{A}(\vec{r},t)$$

Let us look for a solution of the wave equation propagating along $\vec{Oz}$ axis of the form:

$$\vec{A}(\vec{r},t) = \vec{A}_{pol} u(\vec{r}) e^{i(\vec{k}\cdot\vec{z}-\omega t)} \quad (1:3)$$

Replacing in (1:1) and assuming $\vec{A}_{pol}$ independent of space and time, we obtain the equation for the spatial distribution u($\vec{r}$):

$$\frac{\partial^2 u(\vec{r})}{\partial x^2} + \frac{\partial^2 u(\vec{r})}{\partial y^2} + 2ik\frac{\partial u(\vec{r})}{\partial z} = 0 \quad (1:4)$$

Spatial symmetry within the paraxial approximation for Gaussian beams pleads for cylindrical coordinates u($\vec{r}$)=u($\rho,\theta,z$). For Laguerre-Gauss beams, the solution of (1:4) is:

$$u_{l,p}^{LG}(\rho,\theta,z) = \quad (1:5)$$

$$\frac{C_{l,p}}{w(z)} R^{|l|} e^{-\left(\frac{R}{\sqrt{2}}\right)^2} L_p^{|l|}(R^2) e^{-i\left(\frac{kz}{4}\left(\frac{Rw_0}{z_R}\right)^2 + l\theta - (2p+l+1)\arctan\left(\frac{z}{z_R}\right)\right)}$$

with: $C_{l,p} = $ $$\frac{1}{2^{\frac{|l|}{2}} L_p^{|l|}(0)}$$ a normalization constant and $R = R(z) = \frac{\sqrt{2}\rho}{w(z)}$.

For a well-collimated beam (collimation sustained for long distances), one might assume $z_R \gg z$. Taking (1:5) at the limit for $z_R \to \infty$ we find:

$$u_{l,p}^{LG}(\rho,\theta,z) = \frac{C_{l,p}}{w_0} R^{|l|} e^{-\left(\frac{R}{\sqrt{2}}\right)^2} L_p^{|l|}(R^2) e^{-il\varphi} \quad (1:6)$$

The wave equation solution for the potential vector, in cylindrical coordinates, paraxial approximation, Laguerre-Gauss isomorphic is:

$$A(\vec{r}, t) = \qquad (1:7)$$

$$\vec{A}_{pol} u_{l,p}^{LG}(\rho, \theta, z) e^{i(\vec{k} \cdot \vec{z} - \omega t)} = \vec{A}_{pol} \frac{C_{l,p}}{w_0} R^{|l|} e^{-\left(\frac{R}{\sqrt{2}}\right)^2} L_p^{|l|}(R^2) e^{i(kz - \omega t - l\theta)}$$

The potential vector is a function of the radial coordinate ρ through the function:

$$f(R) = f_{l,p}(\rho) = \frac{C_{l,p}}{w_0} R^{|l|} e^{-\left(\frac{R}{\sqrt{2}}\right)^2} L_p^{|l|}(R^2), \qquad (1:8)$$

with $R = R(0) = \frac{\sqrt{2}\rho}{w_0}$

A remarkable and useful solution is the case p=0:

$$f_{l,0}(\rho) = \frac{1}{w_0}\left(\frac{R}{\sqrt{2}}\right)^{|l|} e^{-\left(\frac{R}{\sqrt{2}}\right)^2} = \frac{1}{w_0}\left(\frac{\rho}{w_0}\right)^{|l|} e^{-\left(\frac{\rho}{w_0}\right)^2} \qquad (1:9)$$

Figure 2:
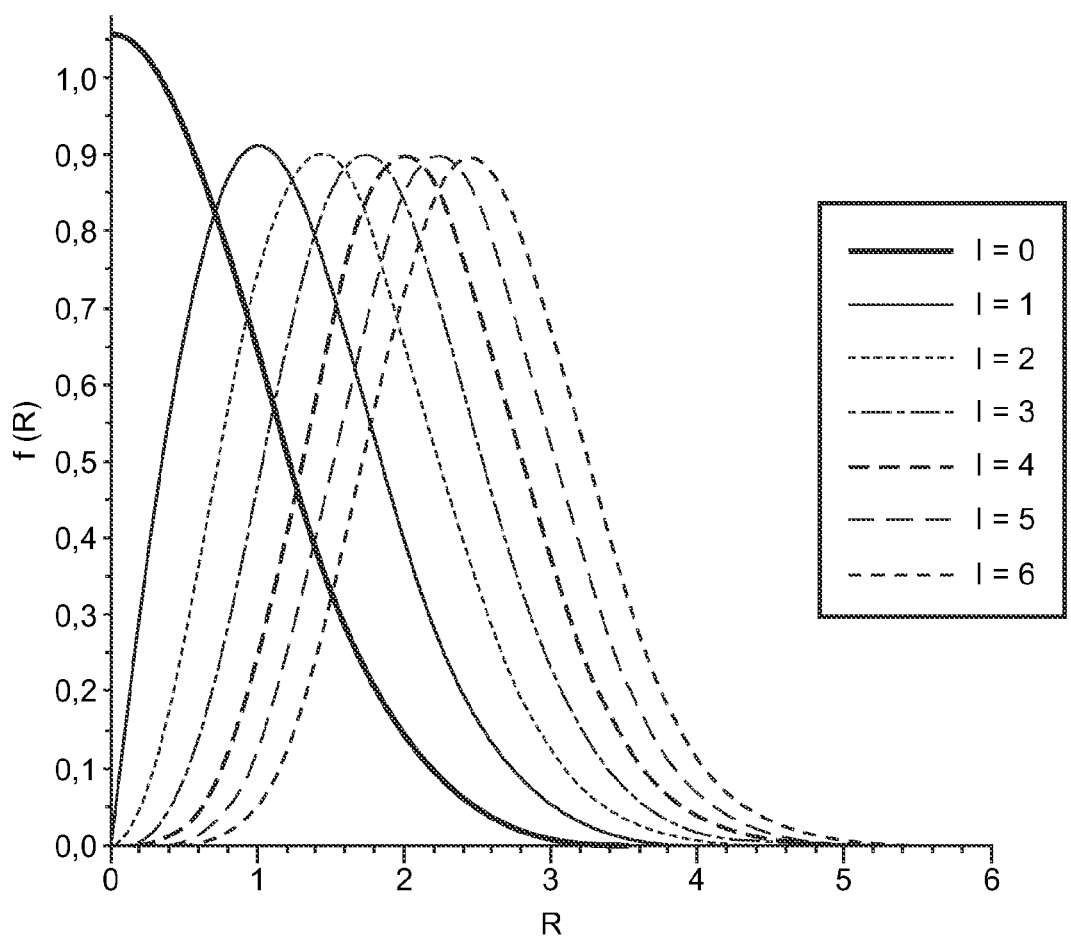
FIG. 2 is a graph showing a potential vector $f$ as a function of a radial coordinate $\rho$.

$f_{l,0}(\rho)$ is 0 for $\rho \in \{0, \infty\}$, has only one maxima for $$R_{max} = \frac{\sqrt{2}\rho_{max}}{w_0} = \sqrt{|l|},$$

and the value at any point is proportional to $1/w_0$. This function does not depend on any physical parameters of the electromagnetic wave (other than $w_0$, and l). FIG. 2 gives the plot for $f(R) = f_{l,0}(\rho)$. In this figure R∈[0,6], l∈{0,6} and $w_0 = 1$. An increase of l leads to an increase of the beam waist with $\sqrt{|l|}$.

Figure 3:
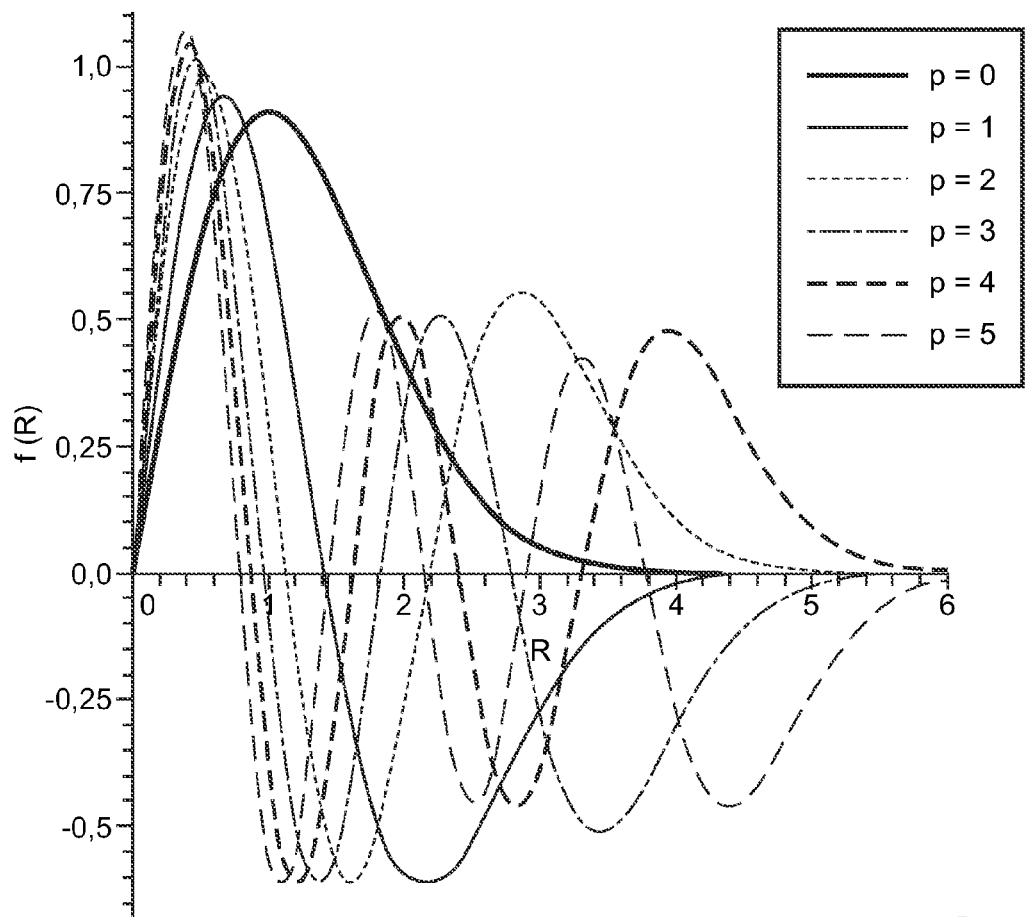
FIG. 3 is a graph showing the potential vector $f$ as a function of the radial coordinate $\rho$ by using other parameters as those used for FIG. 2.

The angular momentum associated to the Laguerre-Gauss beams is $L_z = \|\vec{r} \times \vec{S}\| = l\hbar$. If l is kept constant and p increases as a positive real number, the function $f_{l,p}(\rho)$ has an increasing number of local extreme points. FIG. 3 plots a family of curves with l=1, p∈{0, . . . , 5}, $w_0 = 1$. For this graph, the function $f_{l,p}(\rho)$ has been normalized to $$\sqrt{\int_0^\infty f_{l,p}^2(\rho) d\rho}.$$

It is interesting to note that the gradient increases towards the origin for large p's as well as that the distance between peaks decreases. This marks a change in the sense of the fields for consecutive peaks as well as a higher field gradient for small R's.

From equations (1:2) and (1:7) we can extract the electric and magnetic field strengths:

$$\vec{E}(\vec{r},t) = \vec{E}_{l,p}(\vec{r},t) = \vec{E}_{pol}(\omega) f_{l,p}(\rho) e^{i(kz - \omega t - l\theta)} \qquad (1:10)$$

where: $\vec{E}_{pol}(\omega) = -i\omega \vec{A}_{pol}$. For propagation in isotropic linear media, the electric field strength is a vector parallel to $\vec{A}_{pol}$. This is not the case with the magnetic strength field. Let us choose $\vec{A}_{pol}$ parallel to $\vec{1}_x$. In cylindrical coordinates we obtain:

$$\vec{A}_{pol} = A_{pol} \vec{1}_x = A_{pol,\vec{\rho}} \vec{1}_\rho \qquad (1:11)$$

with: $A_{pol,\vec{\rho}} = A_{pol}$ and $A_{pol,\vec{\theta}} = A_{pol,\vec{z}} = 0$. The gradient operator in cylindrical coordinates is:

$$\nabla = \frac{\partial}{\partial \rho}\vec{1}_\rho + \frac{1}{\rho}\frac{\partial}{\partial \theta}\vec{1}_\theta + \frac{\partial}{\partial z}\vec{1}_z \qquad (1:12)$$

The magnetic field is:

$$\vec{B}(\vec{r}, t) = -\frac{\partial A_{\vec{\rho}}}{\partial z}\vec{1}_\theta - \frac{1}{\rho}\frac{\partial A_{\vec{\rho}}}{\partial \theta}\vec{1}_z \qquad (1:13)$$

with $A_{\vec{\rho}} = A_{pol,\vec{\rho}} f_{l,p}(\rho) e^{i(kz - \omega t - l\theta)}$. Calculations lead to:

$$\vec{B}(\vec{r}, t) = \vec{B}_{l,p}(\vec{r}, t) = iA_{pol,\vec{\rho}} f_{l,p}(\rho) e^{i(kz - \omega t - l\varphi)} \left(-k\vec{1}_\theta + \frac{l}{\rho}\vec{1}_z\right) \qquad (1:14)$$

This relation shows that the magnetic field strength has components not only in $\vec{1}_\theta$ direction, but also in $\vec{1}_z$ direction. The amplitude of the latest direction is proportional to l and decays with the distance from the origin.

The Poynting vector is a classical measure of the energy flux carried by the electromagnetic wave:

$$\vec{S}(\vec{r},t) = \vec{E}(\vec{r},t) \times \vec{B}(\vec{r},t) \qquad (1:15)$$

Looking at the decomposition from (1:3) and (1:12) we obtain:

$$\frac{\vec{S}(\vec{r}, t)}{-i\omega} = A_{\vec{\rho}}\vec{1}_\rho \times \left(\frac{\partial A_{\vec{\rho}}}{\partial z}\vec{1}_\theta + \frac{1}{\rho}\frac{\partial A_{\vec{\rho}}}{\partial \theta}\right) \qquad (1:16)$$

The cylindrical coordinates satisfy $\vec{1}_\rho \times \vec{1}_\theta = \vec{1}_z$, $\vec{1}_z \times \vec{1}_\rho = \vec{1}_\theta$, $\vec{1}_\theta \times \vec{1}_z = \vec{1}_\rho$, and the previous expression for $\vec{S}(\vec{r},t)$ is:

$$\frac{\vec{S}(\vec{r}, t)}{-i\omega} = A_{\vec{\rho}}\frac{1}{\rho}\frac{\partial A_{\vec{\rho}}}{\partial \theta}\vec{1}_\theta + A_{\vec{\rho}}\frac{\partial A_{\vec{\rho}}}{\partial z}\vec{1}_z \qquad (1:17)$$

This shows that there is a flow of electromagnetic energy with two components:

- $\vec{1}_z$ direction component, proportional to the spatial derivative of the potential vector along the beam propagation (as for a plane wave); and
- $\vec{1}_\theta$ direction component, about the axis of the beam propagation. This component is proportional to the angular change of the potential vector around the beam propagation: the Poynting vector rotates about the beam propagation axis.

Let us replace the value of $A_{\vec{\rho}}$ in the last equation:

$$\vec{S}(\vec{r}, t) = \vec{S}_{l,p}(\vec{r}, t) = \omega A_{\vec{\rho}}^2 \left(-\frac{l}{\rho}\vec{1}_\theta + k\vec{1}_z\right) \qquad (1:18)$$

This relation shows that the rotational energy flow is proportional to l. It is interesting to find the ratio of those two components:

$$s_{l,p}^{\theta z}(\vec{r}, t) = \frac{\vec{S}_{l,p}(\vec{r}, t) \cdot \vec{1}_\theta}{\vec{S}_{l,p}(\vec{r}, t) \cdot \vec{1}_z} = -\frac{l}{k\rho} = -\frac{1}{R}\frac{\lambda}{w_0}\frac{l}{\sqrt{2}\pi} \quad (1:19)$$

The ratio $s_{l,p}^{\theta z}(\vec{r},t)$ is time independent. It is also linear with l, therefore the electromagnetic energy flow about the beam propagation axis increases proportional to l. The rotational energy transferred to molecules interacting with light is increased with l. This holds if $\lambda/w_0$ is kept constant for different l's. The magnitude of $s_{l,p}^{\theta z}(\vec{r},t)$ reaches higher values for small $w_0$, which makes the observation of the mentioned dependence easier for tightly focused beams.

Theory: Photon OAM Interactions with Molecules

The manifestation of OAM in the interactions of twisted beams with matter has been explored theoretically, leading to predictions that a light-induced torque can be used to control the rotational motion of atoms. It has been shown that OAM is an intrinsic property of all types of azimuthal phase-bearing light, independent of the choice of axis about which the OAM is defined. The engagement of twisted beam OAM can be classified in terms of intrinsic and extrinsic interactions, i.e. those relating to electronic transitions, and those concerned with centre of mass motion.

On such grounds it might be argued that, in its interaction with an electronically distinct and isolated system such as a free atom or a molecule, intrinsic OAM should manifest through an exchange of orbital angular momentum between the light and matter, just as photon spin angular momentum manifests itself in the selection rules associated with the interactions of circularly polarized light.

It has been further shown that the internal electronic-type motion does not exchange any OAM with the light beam in this leading order of multipole coupling. On detailed analysis, it transpires that only in the weaker electric quadrupole interaction, or in yet higher order multipoles, is there an exchange involving all three subsystems, namely the light, the atomic centre of mass and the internal motion. In the electric quadrupole case, one unit of orbital angular momentum is exchanged between the light beam and the internal motion, resulting in the light beam acquiring of $(l\pm 1)$ OAM, which are then transferred to the centre of mass motion.

Theory: QED Transition Matrix for OAM Beams

Let us consider a molecule made out of $n_{mol}$ particles, with masses $m_n$, charges $e_n$, linear momentum $\vec{p}_n$, spin $\vec{s}_n$, $n \in \{1, \ldots, n_{mol}\}$, $n_e$ electrons and $n_{mol} - n_e$ nucleons.

The molecule interacts with a light beam propagating along Oz axis, with energy $\hbar\omega$, linear momentum $\hbar\vec{k}$ and orbital angular momentum of $\hbar l$. The reference frame origin is chosen at the beam waist of the light beam, as described above.

We will express the transition rate of the molecule from initial state $|i\rangle$ to final state $|f\rangle$, emphasizing the contribution of the orbital angular momentum to this transition. According to Fermi's golden rule, the transition rate $W_{fi}$ (transitions per seconds per molecule) is:

$$W_{fi} = \frac{dP_{fi}}{dt} h|V_{fi}|^2 D(E_{fi}) = h|\langle f|H_{fi}^{(1)}|i\rangle|^2 D(E_{fi}) \quad (3:1)$$

$P_{fi}$ is the probability of the transition from state $|i\rangle$ (energy $E_i$) to state $|f\rangle$ (energy $E_f$) under an electromagnetic excitation defined by the perturbation potential (Hamiltonian) $H_{fi}^{(1)}$ and density of states of $D(E_{fi})$ (where $E_{fi} = E_f - E_i$).

Let us express the matrix element for the transition $M_{fi} = \langle f|H_{fi}^{(1)}|i\rangle$. The Hamiltonian of the molecule-light system is:

$$H(t) = \sum_{n=1}^{n_{mol}} \left[\frac{1}{2m_n}\left(\vec{p}_n - \frac{e_n}{c}\vec{A}(\vec{r}_n, t)\right) \cdot \left(\vec{p}_n - \frac{e_n}{c}\vec{A}(\vec{r}_n, t)\right) - \frac{e_n\hbar}{2m_n c}\left(\vec{s}_n \cdot \nabla_n \times \vec{A}(\vec{r}_n, t)\right)\right] + V_{NN} + V_{NE} + V_{EE} \quad (3:2)$$

with:
$V_{NN}$: Total interaction energy for nucleons;
$V_{NE}$: Total electron-nucleon interaction energy; and
$V_{EE}$: Total interaction energy for electrons.

The "not-perturbed" Hamiltonian includes only terms of the above, which do not depend on the light beam, independent of $\vec{A}(\vec{r}_n, t)$. The expression $H_n(t)$ shown in equation (3:3), describes the energetic interaction of light with each particle that composes the molecule. The Hamiltonian for a particle n interacting with light is:

$$H_n(t) = \frac{1}{2m_n}\left(\vec{p}_n - \frac{e_n}{c}\vec{A}(\vec{r}_n, t)\right) \cdot \left(\vec{p}_n - \frac{e_n}{c}\vec{A}(\vec{r}_n, t)\right) - \frac{e_n\hbar}{2m_n c}\left(\vec{s}_n \cdot \nabla_n \times \vec{A}(\vec{r}_n, t)\right) == \quad (3:3)$$

$$\frac{1}{2m_n}\left(\vec{p}_n \cdot \vec{p}_n - \frac{e_n}{c}\left(\vec{A}(\vec{r}_n, t) \cdot \vec{p}_n + \vec{p}_n \cdot \vec{A}(\vec{r}_n, t)\right) + \left(\frac{e_n}{c}\right)^2 \vec{A}(\vec{r}_n, t) \cdot \vec{A}(\vec{r}_n, t)\right) - \frac{e_n\hbar}{2m_n c}\left(\vec{s}_n \cdot \nabla_n \times \vec{A}(\vec{r}_n, t)\right)$$

Because of the QED rule that the potential acts only once, the term $\vec{A}(\vec{r}_n,t) \cdot \vec{A}(\vec{r}_n,t)$ does not enter this problem. With $$\mu_n = \frac{e_n\hbar}{2m_n c}$$

(for an electron, $\mu_n$ represents the "Bohr magneton") and replacing the linear momentum vector with its quantum operator $\vec{p}_n \to i\hbar\nabla_n$, the Hamiltonian turns into:

$$\hat{H}_n(t) = \underbrace{-\frac{\hbar^2}{2m_n}|\nabla_n|^2}_{\hat{H}_n^{(0)}} \quad (3:4)$$

$$\underbrace{-i\mu_n\left[\vec{A}(\vec{r}_n, t) \cdot \nabla_n + \nabla_n \cdot \vec{A}(\vec{r}_n, t) + \vec{s}_n \cdot \nabla_n \times \vec{A}(\vec{r}_n, t) + \vec{s}_n \cdot \nabla_n \times \vec{A}(\vec{r}_n, t)\right]}_{\hat{H}_{int,n}(t) = \hat{H}_n^{(1)}}$$

The $^{(0)}$ index marks the time independent Hamiltonian, while the $^{(1)}$ index represents the light-molecule interaction Hamiltonian (perturbation).

$$\hat{H}^{(0)} = V_{NN} + V_{EE} + V_{NE} + \sum_{n=0}^{n_{mol}} \hat{H}_n^{(0)} \quad (3:5)$$

$$\hat{H}^{(1)} = \hat{H}^{(1)}(t) = \sum_{n=0}^{n_{mol}} \hat{H}_n^{(1)}$$

The time dependent Schrödinger equation is:

$$i\hbar\frac{\partial}{\partial t}\Psi(\vec{r},t) = [H^{(0)} + H^{(1)}(t)]\Psi(\vec{r},t) \quad (3:6)$$

With the stationary states eigenfunctions $\psi_k$ and eigenvalues $E_k$ satisfying:

$$H^{(0)}\psi_k = E_k\psi_k, k\in\{1,\ldots,N\} \quad (3:7)$$

And a general solution of $$\Psi(\vec{r},t) = \sum_k c_k(t)\psi_k(\vec{r})e^{-\frac{i}{\hbar}E_k t} \quad (3:8)$$

The first order perturbation theory gives:

$$\frac{dc_b(t)}{dt} = \frac{1}{i\hbar}\sum_{k=0}^{N} H_{b\leftarrow k}^{(1)}(t)c_k(t)e^{i\omega_{bk}t} \quad (3:9)$$

with: $H_{b\leftarrow k}^{(1)}(t) = \langle_b|H_{bk}^{(1)}(t)|_k\rangle$ and $\omega_{bk} = (E_b-E_k)/\hbar$. Initial conditions assume that before the interaction the molecule is in state $\Psi(\vec{r},t\leq0)=\psi_a$ ($c_a^{(0)}=1$) and the final state $\psi_b$ is not occupied ($c_b^{(0)}=0$). Replacing those in (3:9) we obtain $c_k(t\leq0) = c_k^{(0)}\delta_{ka}$, ($\delta_{ka}$: Kronecker symbol) and $$\frac{dc_b(t)}{dt} = \quad (3:10)$$

$$\frac{1}{i\hbar}H_{b\leftarrow a}^{(1)}(t)\delta_{ka}e^{i\omega_{ba}t} \Leftrightarrow c_b(t) = \frac{1}{i\hbar}\int_0^t H_{b\leftarrow a}^{(1)}(\tau)e^{i\omega_{ba}\tau}d\tau - c_b^{(0)}$$

We will express the time dependent perturbation $H_{b\leftarrow a}^{(1)}(\tau)$ for a Laguerre-Gauss (LG) beam. From (3:4), the electromagnetic interaction perturbation Hamiltonian for a particle n is:

$$\hat{H}_n^{(1)} = -i\mu_{Bn}[\vec{A}(\vec{r}_n,t)\cdot\nabla_n + \nabla_n\cdot\vec{A}(\vec{r}_n,t) + \vec{s}_n\cdot\nabla_n\times A(\vec{r}_n,t)] \quad (3:11)$$

Apply a variable separation (time) for the equations describing the LG wave (1:10-1:14):

$$F_{l,p}(\vec{r}_n) = A_{pol,\rho}f_{l,p}(\rho_n)e^{i(kz_n - l\theta_n)} \quad (3:12)$$

$$\vec{A}(\vec{r}_n,t) = F_{l,p}(\vec{r}_n)e^{-i\omega t}\vec{1}_\rho$$

$$\vec{B}(\vec{r}_n,t) = iF_{l,p}(\vec{r}_n)\left(-k\vec{1}_\theta + \frac{l}{\rho_n}\vec{1}_z\right)e^{-i\omega t}$$

Since the field is not uniform, the Coulomb Gauge does not apply:

$$\nabla_n\cdot\vec{A}(\vec{r}_n,t\neq 0) \quad (3:13)$$

After some algebra involving the expression for $\nabla_n$ in cylindrical coordinates, the Hamiltonian operator becomes:

$$\hat{H}_n^{(1)}(t) = \hat{H}_n^{(1)}e^{-i\omega t} = \quad (3:14)$$

$$i\mu_n F_{l,p}(\vec{r}_n)\left[\frac{\partial}{\partial\rho_n} + \frac{1}{F_{l,p}(\vec{r}_n)}\frac{\partial F_{l,p}(\vec{r}_n)}{\partial\rho_n} + k\vec{s}_n\cdot\vec{1}_\theta - \frac{l}{\rho_n}\vec{s}_n\cdot\vec{1}_z\right]e^{-i\omega t}$$

$\hat{H}_n^{(1)}$ is the time independent operator associated to the perturbed Hamiltonian. From (3:9) and (3:15) one can find the value of the transition probability as:

$$c_b(t) = \frac{1}{i\hbar}\sum_{n=1}^{n_{mol}}\int_0^\infty\left(\langle b|H_n^{(1)}|a\rangle\int_0^\tau e^{i(\omega_{ba}-\omega)\tau}d\tau + h.c.\right)d\omega \quad (3:15)$$

h.c. is the complex harmonic conjugate of the transition matrix:

$$h.c. = \langle b|H_n^{(1)*}|a\rangle\int_0^t e^{i(\omega_{ba}+\omega)\tau}d\tau + h.c. \quad (3:16)$$

Photon absorption occurs when the final energy of the molecule exceeds the initial value ($\omega_{ba}\geq 0$). This condition nulls the h.c. term. The transition probability for absorption is proportional to:

$$\|c_b(t)\|^2 = \left\|\frac{1}{\hbar}\sum_{n=1}^{n_{mol}}\int_0^\infty\langle b|H_n^{(1)}|a\rangle\int_0^t e^{i(\omega_{ba}-\omega)\tau}d\tau\cdot d\omega\right\|^2 \quad (3:17)$$

We can simplify this expression further, by observing that the absolute value of the exponential function integral in (3:17) is approximately null except for frequencies close to $\omega_{ba}$. The matrix element in the previous formula has meaningful values only around $\omega \; \omega_{ba}$:

$$\|c_b(t)\|^2 = \left\|\frac{1}{\hbar}\sum_{n=1}^{n_{mol}}\int_0^\infty\langle b|H_n^{(1)}|a\rangle\int_0^t e^{i(\omega_{ba}-\omega)\tau}d\tau\cdot d\omega\right\|^2 \quad (3:18)$$

The time and frequency double integral yields:

$$\|\int_{-\infty}^\infty\int_0^t e^{i(\omega_{ba}-\omega)\tau}d\tau\cdot d\omega\|^2 = \pi t \quad (3:19)$$

We then obtain a general result: the probability for the system to be in the state b at time t, assuming that a is the initial state of the system equals:

$$\|c_b(t)\|^2 = \frac{\pi}{\hbar^2}\left\|\sum_{n=1}^{n_{mol}}\langle b|H_n^{(1)}|a\rangle|_{\omega=\omega_{ba}}\right\|^2 t \quad (3:20)$$

With (3:1), the transition rate is:

$$W_{fi} = \frac{dP_{fi}}{dt} = h|V_{fi}|^2 D(E_{fi}) = \frac{2\pi^2}{\hbar}\left\|\sum_{n=1}^{n_{mol}}\langle f|H_n^{(1)}|i\rangle\right\|_{\omega=\omega_{fi}}^2 \quad (3:21)$$

$$D(E_{fi})$$

Therefore, the matrix element is expressed for every particle involved in the photon absorption process, and the absolute value of their sum is calculated.

The matrix element for particle n (first order perturbation theory) is:

$$M_{n,f \leftarrow i,l,p} = -i\mu_n \qquad (3:22)$$

$$\left\langle f \left| F_{l,p}(\vec{r}_n) \left( \frac{\partial}{\partial \rho_n} + \frac{1}{F_{l,p}(\vec{r}_n)} \frac{\partial F_{l,p}(\vec{r}_n)}{\partial \rho_n} + k \vec{s}_n \cdot \vec{1}_\theta - \frac{l}{\rho_n} \vec{s}_n \cdot \vec{1}_z \right) \right| i \right\rangle$$

This result is exact.
Theory: Transition Matrix Interpretation
The matrix element is a sum of 4 terms:

$$M^I_{n,f \leftarrow i,l,p} = -i\mu_n \left\langle f \left| F_{l,p}(\vec{r}_n) \frac{\partial}{\partial \rho_n} \right| i \right\rangle \qquad (4:1)$$

$$M^{II}_{n,f \leftarrow i,l,p} = -i\mu_n \left\langle f \left| \frac{\partial F_{l,p}(\vec{r}_n)}{\partial \rho_n} \right| i \right\rangle$$

$$M^{III}_{n,f \leftarrow i,l,p} = -i\mu_n k \left\langle f \left| F_{l,p}(\vec{r}_n) \vec{s}_n \cdot \vec{1}_\theta \right| i \right\rangle$$

$$M^{IV}_{n,f \leftarrow i,l,p} = i\mu_n l \left\langle f \left| \frac{F_{l,p}(\vec{r}_n)}{\rho_n} \vec{s}_n \cdot \vec{1}_z \right| i \right\rangle$$

Transition $M^I_{n,f \leftarrow i,l,p}$

The first term, $M^I_{n,f \leftarrow i,l,p}$ describes the kinetic energy contribution of a particle.

$$\left. \begin{array}{l} F_{l,p}(\vec{r}_n) = f_{l,p}(\rho_n) e^{i(kz_n - l\theta_n)} \\ M^I_{n,f \leftarrow i,l,0} = -i\mu_n \left\langle f \left| F_{l,p}(\vec{r}_n) \frac{\partial}{\partial \rho_n} \right| i \right\rangle \end{array} \right\} \Rightarrow \qquad (4:2)$$

$$\left. \begin{array}{l} M_{n,f \leftarrow i,l,p} = -i\mu_n \left\langle f \left| f_{l,p}(\rho_n) e^{i(kz_n - l\theta_n)} \frac{\partial}{\partial \rho_n} \right| i \right\rangle \\ e^{i(kz_n - l\theta_n)} = e^{-il\theta_n} \sum_{q=0}^{\infty} \frac{1}{q!} (ikz_n)^q \approx e^{-il\theta_n} \end{array} \right\} \Rightarrow$$

$$M^I_{n,f \leftarrow i,l,0} = -i\mu_n \left\langle f \left| f_{l,p}(\rho_n) e^{-il\theta_n} \frac{\partial}{\partial \rho_n} \right| i \right\rangle$$

$M^I_{n,f \leftarrow i,l,0}$ is proportional to $$f_{l,0}(\rho) = \frac{1}{w_0} \left( \frac{\rho}{w_0} \right)^{|l|} e^{-\left( \frac{\rho}{w_0} \right)^2}$$

and the non-uniformity of the molecule in the plane perpendicular to the beam propagation.

Let us observe the influence of $w_0$, which represents the beam waist:

for a large $$w_0, \lim_{w_0 \to \infty} (M^I_{n,f \leftarrow i,l,0}) \to 0;$$

for small $$w_0, \lim_{w_0 \to 0} (M^I_{n,f \leftarrow i,l,0}) \to 0;$$

maximum of $M^I_{n,f \leftarrow i,l,0}$ occurs for $$\frac{\partial M^I_{n,f \leftarrow i,l,0}}{\partial w_0} = 0 \text{ at } w_0 = \rho \sqrt{2/(1+|l|)};$$

and
maximum of $M^I_{n,f \leftarrow i,l,0}$ occurs for $$\frac{\partial M^I_{n,f \leftarrow i,l,0}}{\partial \rho} = 0 \text{ at } \rho = w_0 \sqrt{l/2}.$$

One could conclude that the maximum observable effect area is given by the Airy disk:

1. The probability of OAM interaction with molecules is zero at spatial points placed far from the centre of the light beam or in the centre of the light beam.
2. The probability of OAM interaction with molecules reaches maximum at spatial points placed at $\rho = w_0 \sqrt{l/2}$.
3. The probability of OAM interaction with molecules reaches maximum at spatial points placed at $w_0 = \rho \sqrt{2/(1+|l|)}$.
4. Maximum interaction probability occurs on the radius corresponding to the maximum field distribution, for circles close to the Airy disk.

Transition $M^{II}_{n,f \leftarrow i,l,p}$

The second term, $M^{II}_{n,f \leftarrow i,l,p}$ $$\left. \begin{array}{l} M^{II}_{n,f \leftarrow i,l,p} = -i\mu_n \left\langle f \left| \frac{\partial F_{l,p}(\vec{r}_n)}{\partial \rho_n} \right| i \right\rangle \\ F_{l,p}(\vec{r}_n) = f_{l,p}(\rho_n) e^{i(kz_n - l\theta_n)} \end{array} \right\} \Rightarrow \qquad (4:3)$$

$$M^{II}_{n,f \leftarrow i,l,p} = -i\mu_n \left\langle f \left| \frac{\partial f_{l,p}(\rho_n)}{\partial \rho_n} e^{i(kz_n - l\theta_n)} \right| i \right\rangle$$

$f_{l,p}(\rho_n)$ is given by (1:8) with $R_n = \sqrt{2}\rho_n/w_0$. The radial derivative of $f_{l,p}(\rho_n)$ is:

$$\frac{\partial f_{l,p}(\rho_n)}{\partial \rho_n} = \frac{C_{l,p}}{w_0} \frac{\partial \left( R_n^{|l|} e^{-\left( \frac{R_n}{\sqrt{2}} \right)^2} L_p^{|l|}(R_n^2) \right)}{\partial R_n} \frac{\partial R_n}{\partial \rho_n} \Leftrightarrow \qquad (4:4)$$

$$\frac{\partial f_{l,p}(\rho_n)}{\partial \rho_n} = \frac{C_{l,p}}{w_0} \frac{\sqrt{2}}{w_0} \left( \frac{|l|}{R_n} R_n^{|l|} e^{-\left( \frac{R_n}{\sqrt{2}} \right)^2} L_p^{|l|}(R_n^2) - \right.$$

$$\left. R_n R_n^{|l|} e^{-\left( \frac{R_n}{\sqrt{2}} \right)^2} L_p^{|l|}(R_n^2) + R_n^{|l|} e^{-\left( \frac{R_n}{\sqrt{2}} \right)^2} \frac{\partial L_p^{|l|}(R_n^2)}{\partial R_n} \right)$$

From orthogonal polynomial recurrence properties one can calculate the derivative for a Laguerre polynomial as:

$$\frac{\partial L_p^{|l|}(R_n^2)}{\partial R_n} = \frac{2}{R_n} \left( p L_p^{|l|}(R_n^2) - (p+|l|) L_{p-1}^{|l|}(R_n^2) \right) \qquad (4:5)$$

Replacing the latest in the formula for $f_{l,p}(\rho_n)$ radial derivative we obtain:

$$\frac{\partial f_{l,p}(\rho_n)}{\partial \rho_n} = f_{l,p}(\rho_n) \frac{\sqrt{2}}{w_0} \frac{1}{R_n}\left(|l| + 2p - R_n^2 - 2(|l|+p)\frac{L_{p-1}^{|l|}(R_n^2)}{L_p^{|l|}(R_n^2)}\right) \quad (4:6)$$

Using Laguerre polynomial recurrence definition (1:8) we express the order p−1 as a function of order p:

$$L_p^{|l|}(R_n^2) = \sum_{m=0}^{p-1}(-1)^m \frac{(p+|l|)!}{(p-m)!(|l|+m)!m!} R_n^{2m} + \quad (4:7)$$

$$(-1)^p \frac{(p+|l|)!}{(p-p)!(|l|+p)!p!} R_n^{2p} \Leftrightarrow$$

$$\frac{L_{p-1}^{|l|}(R_n^2)}{L_p^{|l|}(R_n^2)} = 1 - \frac{(-1)^p}{p!} \frac{R_n^{2p}}{L_p^{|l|}(R_n^2)}$$

This finally leads to:

$$\frac{\partial f_{l,p}(\rho_n)}{\partial \rho_n} = \quad (4:8)$$

$$f_{l,p}(\rho_n)\frac{\sqrt{2}}{w_0}\frac{1}{R_n}\left(|l| + 2p - R_n^2 - 2(|l|+p)\left(1 - \frac{(-1)^p}{p!}\frac{R_n^{2p}}{L_p^{|l|}(R_n^2)}\right)\right) \Leftrightarrow$$

$$\frac{\partial f_{l,p}(\rho_n)}{\partial \rho_n} = f_{l,p}(\rho_n)\frac{\sqrt{2}}{w_0}\left(-\frac{|l|}{R_n} - R_n + \frac{(-1)^p 2(|l|+p)}{p!}\frac{R_n^{2p-1}}{L_p^{|l|}(R_n^2)}\right)$$

The matrix element is:

$$M_{n,f \leftarrow i,l,p}^{II} = i\mu_n \frac{\sqrt{2}}{w_0}\left[-|l|\left\langle f\left|\frac{F_{l,p}(\vec{r}_n)}{R_n}\right|i\right\rangle - \right. \quad (4:9)$$

$$\left\langle f\left|R_n F_{l,p}(\vec{r}_n)\right|i\right\rangle + \frac{(-1)^p 2(|l|+p)}{p!}\left\langle f\left|\frac{R_n^{2p-1}}{L_p^{|l|}(R_n^2)}F_{l,p}(\vec{r}_n)\right|i\right\rangle\right]$$

Let's simplify it for the particular case of p=0:

$$M_{n,f \leftarrow i,l,0}^{II} = i\mu_n \frac{\sqrt{2}}{w_0}\left(|l|\left\langle f\left|\frac{F_{l,0}(\vec{r}_n)}{R_n}\right|i\right\rangle - \left\langle f\left|R_n F_{l,0}(\vec{r}_n)\right|i\right\rangle\right) \quad (4:10)$$

It shows the matrix element $M_{n,f \leftarrow i,l,p}^{II}$ is linearly dependent on l.

Transition $M_{n,f \leftarrow i,l,p}^{III}$

The third term is:

$$M_{n,f \leftarrow i,l,p}^{III} = -i\mu_n k\langle f|F_{l,p}(\vec{r}_n)\vec{s}_n \cdot \vec{1}_\theta|i\rangle \quad (4:11)$$

The matrix element $M_{n,f \leftarrow i,l,p}^{III}$ represents the interaction of the OAM with electron (and nucleon) spin.

Transition $M_{n,f \leftarrow i,l,p}^{IV}$

The fourth term is of a major interest, since it depicts a linear dependence of a transition probability on a parameter of the incident light, other than frequency or spin:

$$M_{n,f \leftarrow i,l,p}^{IV} = \quad (4:12)$$

$$\mu_n l\left\langle f\left|\frac{F_{l,p}(\vec{r}_n)}{\rho_n}\vec{s}_n \cdot \vec{1}_z\right|i\right\rangle = i\mu_n l\left\langle f\left|\frac{F_{l,p}(\vec{r}_n)}{\rho_n}(\vec{L}_n + \vec{\sigma}_n)\cdot\vec{1}_z\right|i\right\rangle =$$

$$i\mu_n l\left(\left\langle f\left|\frac{F_{l,p}(\vec{r}_n)}{\rho_n}\vec{L}_n \cdot \vec{1}_z\right|i\right\rangle + \left\langle f\left|\frac{F_{l,p}(\vec{r}_n)}{\rho_n}\vec{\sigma}_n \cdot \vec{1}_z\right|i\right\rangle\right) =$$

$$i\mu_n l\left(\left\langle f\left|M_{n,f \leftarrow i,l,p}^{II}\vec{L}_{n,\vec{1}_z}\right|i\right\rangle + \left\langle f\left|\frac{F_{l,p}(\vec{r}_n)}{\rho_n}\vec{\sigma}_n \cdot \vec{1}_z\right|i\right\rangle\right)$$

$M_{n,f \leftarrow i,l,p}^{IV}$ shows that there is an interaction of the light carrying OAM with the kinetic momentum $L_{n,\vec{1}_z}$ component parallel to the direction of the light beam $\vec{1}_z$. This interaction is proportional to the OAM of light/and is more probable for low $\rho_n$ (beam waist close to the minimum of the diffraction limited Airy disk). Same comments apply for the interaction of light carrying spin $\vec{\sigma}_n$ with the electron magneton.

This is the basis for producing fluid with hyperpolarization along the direction $\vec{1}_z$ of the propagation of the light beam.

The formulae above show that there is an interaction of the momenta carried by light with all types of spins and orbital momenta carried by molecule constituents.

The same formulae also show that in some cases, the transition matrix coefficients are proportional to l, therefore a higher interaction is probable for light carrying large OAM.

The transition matrix coefficients $M_{n,f \leftarrow i,l,p}^{II}$ and $M_{n,f \leftarrow i,l,p}^{IV}$ include terms proportional to $$\frac{1}{R_n} \text{ and } \frac{1}{\rho_n},$$

meaning that these coefficients reach higher values for small $R_n$ and $\rho_n$. Given the "maximum observable effect area" criteria from the previous section, the maximum value of the transition matrix coefficients $M_{n,f \leftarrow i,l,p}^{II}$ and $M_{n,f \leftarrow i,l,p}^{IV}$ is obtained with a light beam with the radius as close as possible to the Airy disk radius.

These coefficients apply for photon-molecule absorption, emission and quasi-transitions.

These coefficients refer to the gross selection rules, which are statements about the properties that a molecule must possess in order for it to be capable of showing a particular type of transition.

Figure 4:
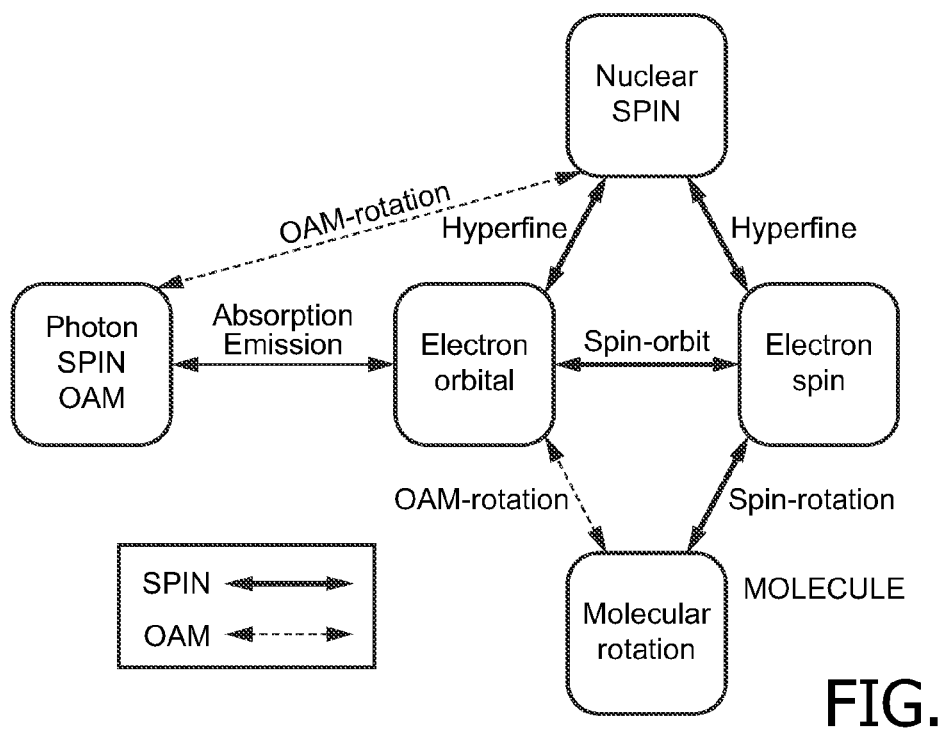
FIG. 4 shows possible OAM-molecule interactions.

The specific selection rules (the changes in quantum numbers that may occur during such transitions) are not predicted by this theory, but are qualitatively mentioned in FIG. 4.

Specific Selection Rules for Molecule-Light Interactions Absorption

Light carrying spin $\vec{\sigma}_n$ and OAM l is absorbed by molecules. As angular momentum is a conserved quantity, the total angular momentum of the system (radiation and matter) cannot be changed during absorption and emission of radiation. When a photon is absorbed by an atom or molecule, its angular momentum has to be therefore transferred to the atom. The resulting angular momentum of the atom then equals to the vector sum of its initial angular momentum plus the angular momentum of the absorbed photon.

Atoms and molecules may contain different types of angular momenta. The most important reservoirs include orbital angular momentum of electrons, rotational motion of molecules and spin angular momentum of electrons and nuclei. Not all these types of angular momenta couple directly to the radiation field: in free atoms, only the orbital angular momentum of the electrons is directly coupled to the optical transitions. However, the different types of angular momenta are in general coupled to each other by various interactions which allow the polarization to flow from the photon spin reservoir through the electron orbital to all the other reservoirs, as shown schematically in FIG. 4.

Above it was demonstrated theoretically the possibility of OAM—molecule interaction that made possible the OAM-rotation transitions shown in FIG. 4. It was also demonstrated that the interaction is proportional to the value of the OAM carried by the light beam.

Therefore, it is probable (proportional to l) to:
  Transfer/align not only the electronic spin population of orbitals excited during absorption processes, but also the OAM of the molecule.
  Change the molecular rotation value and orientation towards momenta parallel to the beam axis propagation (on the periphery of the Airy disk).
  Direct transfer/align molecule nuclei.
  Transparent Molecules These are cases of "quasi-transitions", where photons interact with orbitals, but do not have enough energy to produce an excited molecular state. The photon is absorbed and emitted by the molecule almost at the same time (short "quasi-state" life time). There are changes within the incident and emitted photons momenta and energies (e.g. Raman back scattering). Therefore, light with OAM will interact with transparent molecules as well, transferring the photon angular momenta to the rotational momentum of the molecule.

We can conclude that molecules' momenta are changed, i.e. aligned in direction to the incident beam propagation axis and modified in magnitude, by light endowed with spin and OAM, proportional to the OAM content of light.

The optical pumping shows that molecules can be hyperpolarized with light carrying spin (circular polarized light). The method has been successfully used for obtaining hyperpolarized gases, with applications in MRI.

The present invention adds the photons an OAM, therefore increases the orientation of the molecular momenta along the direction of propagation of the light and increases the probability of obtaining hyperpolarized molecules within fluids. Hence, an NMR analysis of the fluid is possible.

This concept has been experimentally proven by a laboratory setup, which will be described next.

Laboratory Setup Description

Figure 5:
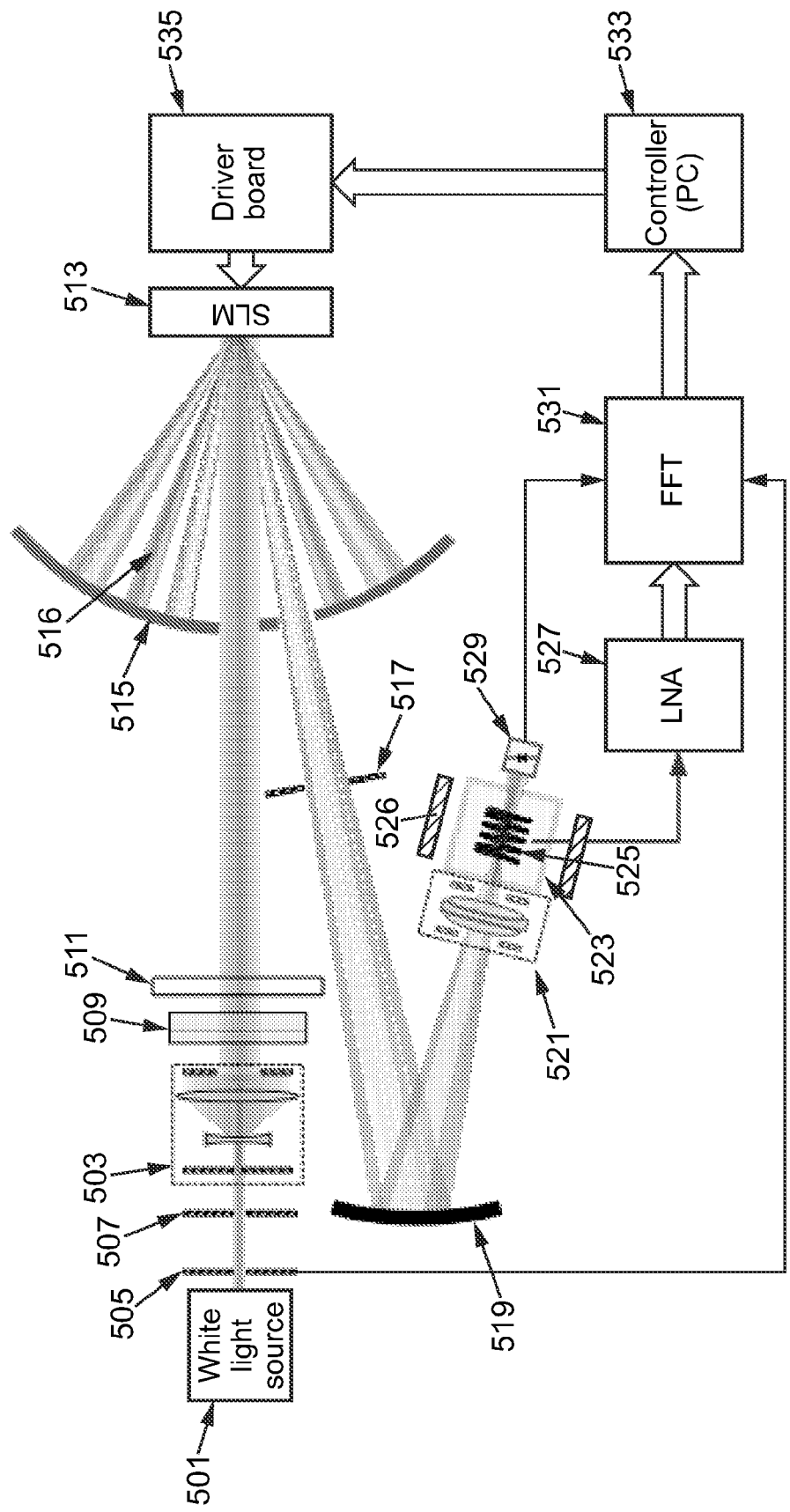
FIG. 5 is a block diagram of a laboratory setup for carrying out fluid analysis in accordance with an embodiment of the present invention.

FIG. 5 shows an exemplary setup for analyzing fluids in accordance with the teachings of the present invention. The white light is produced with an HP Mercury, 100 W white light source 501, and is collimated so that the diameter of the beam is roughly 1 mm. The collimated light, i.e. the beam, is then sent to a beam expander (1:20) 503. Between the beam expander 503 and the light source 501 there is a mechanical shutter 505, in this case a rotating wheel, which is capable of generating an electrical signal synchronized to the opening of the shutter. There is also a manual shutter 507, while the mechanical shutter 505 is operational. This shutter blocks the light while measurements are performed in "dark" states, while the entire system operates as in "light" conditions, and it is required for maintaining the same noise environment for all measured states. After passing through the beam expander 503, the light is circularly polarized with a linear polarizer 509 followed by a quarter wave plate 511.

A space light modulator (SLM) 513, in this case a liquid crystal on silicon (LCoS) panel, 1280×720, 20×20 μm$^2$, 45TN LC effect, 1 μm cell gap produces a computer generated phase hologram designed to change the Gaussian incident beam to a Laguerre Gaussian (LG) beam, carrying OAM and spin. The value l of the OAM is a parameter of the hologram and can be increased to values up to 40, but cannot be easily further increased due to practical issues related to spatial filtering.

Figure 6:
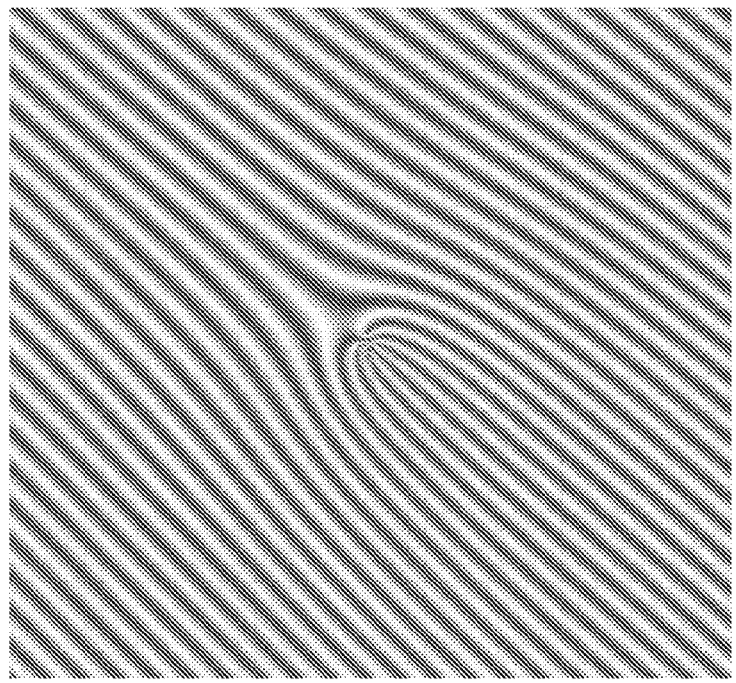
FIG. 6 shows a computer generated phase hologram displayed on a spatial light modulator panel.
Figure 7:
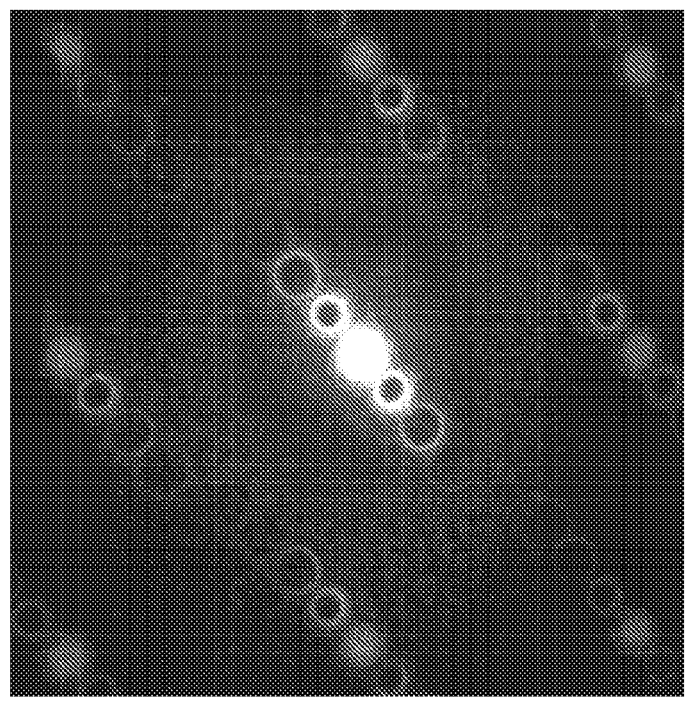
FIG. 7 shows a hologram projection on a screen placed three meters apart from the spatial light modulator.

FIG. 6 shows the computer generated phase hologram that has been displayed on the SLM panel with the following parameters l=10, $w_s$=5 and p=0, while FIG. 7 represents the hologram projection with an incident HeNe laser (618 nm) on a screen 515 placed at roughly 3 m from the SML 513. The bright spot in the middle of this figure represents the zero$^{th}$ order diffraction carrying no OAM while the circles in the north west and south east directions from it are generated by LG mode beams carrying OAM with l={10, 11, 12 . . . } and l={−10, −11, −12 . . . } respectively.

When the same hologram is irradiated with different wave lengths, the zero$^{th}$ order diffraction spot conserves its position, whereas its adjacent LG diffracted beams obey the normal diffraction grating dispersions laws. The same hologram produces LG beams carrying OAM of {±l, ±(l+1), ±(l+2) . . . } for different wavelengths.

Figure 8:
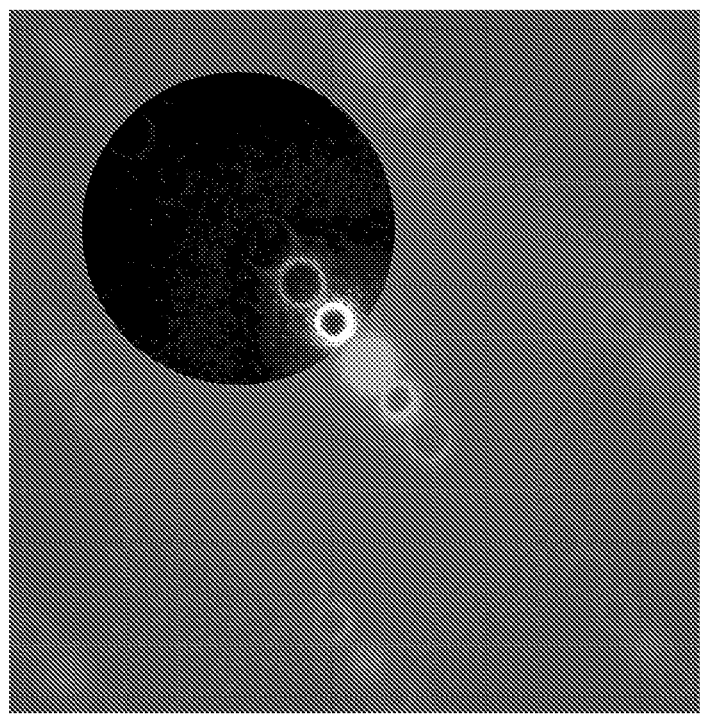
FIG. 8 shows a projection of selected Laguerre Gaussian diffracted orders after spatial filtering.

In the laboratory setup a screen, i.e. spatial filter 517, was used to block the zero$^{th}$ order and the diffracted LG beams were selected that carry OAM and spin. The result is shown in FIG. 8.

The dispersed diffracted LG beams are collected and focused onto the sample by use of a concave mirror 519 and a fast microscope objective 521. The high $f_\#$ is required in order to satisfy the condition of a beam waist as close as possible to the Airy disk size.

Figure 9:
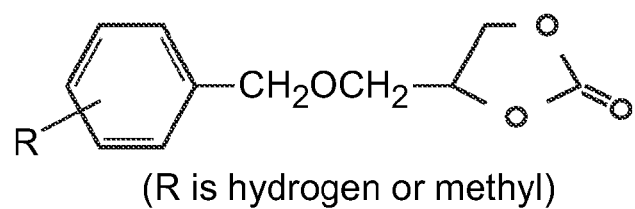
FIG. 9 shows the chemical structure of the sample used in an exemplary embodiment for which a free induction decay (FID) signal can be obtained.

After passing through the objective, we obtained a tightly focused beam of white light carrying spin (circular polarization) and OAM of l=19. The beam is then applied to a fluid sample located in a sample cuvette 523. For this experiment optical oil with a structure shown in FIG. 9 was chosen.

The irradiated sample is surrounded by a fluid submerged copper coil 525, which has the following characteristics in this example: inner diameter 2 mm, outer diameter 10 mm, coil length 10 mm, diameter of the copper windings 0.75 mm. The coil 525 is electrically connected to an input of a 50 low noise amplifier (LNA) 527 with a 50 MHz bandwidth, high pass filter at 5 KHz and gain of 40 dB.

The amplified output, i.e. a voltage proportional to the voltage at the coil terminals, therefore proportional to the magnetic flux variation through the coil, is recorded by a measurement device, in this case a Tektronix TDK 700 series scope, on a 5 mV input scale range, 25 MHz sampling frequency, 20 MHz input low pass filter (LPF), resolution of 16 bits (high resolution), real time acquisition, 200K samples.

Figure 10:
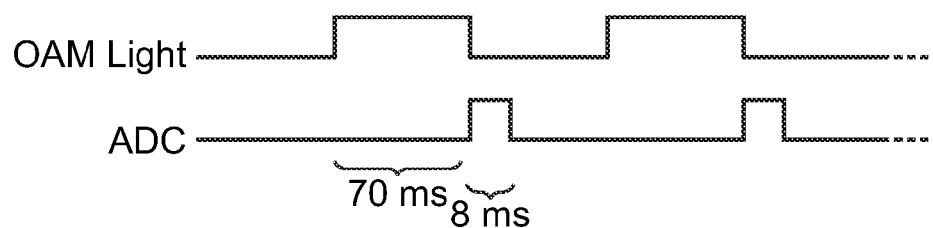
FIG. 10 shows the used light pulse drawn along a time line and the obtained digital FID signal.

In FIG. 5 there is also shown an electromagnetic magnet 526 for creating a magnetic field around the sample. This magnet is used for directing the light beam so that the nuclear magnetic polarizability induced in the sample can be changed. A static magnetic field can thus be applied to the sample such that the orientation of the B field is perpendicular to the OAM light beam's direction of propagation. In the initial experiments, a 0.1 Tesla field was used. The magnetic field helps to create an organized FID when the OAM light is switched off as shown in FIG. 10. From this figure it can be seen that once the light is turned off, the resulting FID signal is then sampled using an analog to digital converter (ADC). The trigger event has been provided by the synchronization output of the mechanical shutter 505. The photo diode (pin device), i.e. the photo detector 529 in FIG. 5, has been used as a trigger signal delay estimation device. It measures the delay between the synchronization signal generated by the mechanical shutter 505 and the raise time of the light passing thorough the sample. This value is measured once and used as the trigger delay value for the rest of the measurements.

The acquired data set is passed to a fast Fourier transformer (FFT) 531 which performs the FFT algorithm (Hamming window, −35 dB phase rejection, and average factor of 20), which produces the amplitude for the frequency domain of the free induction decay (FID) signal. In FIG. 5 there is also shown a controller unit 533, which can be a personal computer (PC) for processing the obtained FID signal. The controller unit 533 may be connected to a driver board 535, which controls the operation of the SLM unit 513.

The data acquisition setup summary is given in Table 2. The acquisition time and number of samples shall be improved in experiments seeking the determination of chemical species present within the fluid sample. For the purpose of a proof of concept, the setup explained above is sufficient, since it depicts a clear difference between the FID spectrums for the sample irradiated by light with OAM vs. the sample irradiated by light with no OAM (l=0) and the sample that is not irradiated by any light (perpendicular B field is still present).

TABLE 2

| LNA GAIN [dB] | Nr. Samples [ ] | Input Sensitivity [mV] | Input Bandwidth [MHz] | Sample Speed [Msamples/s] | Acquisition Time [µs] |
|---|---|---|---|---|---|
| 40 | 5000 | 5 | 20 | 25 | 200 |

Experiment Flow Description

The setup described above allows the acquisition of the magnetic FID of a sample illuminated with light with spin and an OAM of 10 ℏ and comparing it with the same FID coming from the not illuminated sample. The last case might seem unnecessary, since the FID of an unpolarized sample shall produce amplitudes below the noise level of the acquisition system. However, generating the difference between the illuminated and "dark" sample is beneficial in order to reduce all ergodic environment noise sources. Along the same line, the "dark" measurement is performed by closing the manual shutter 507 only (the light source and mechanical shutter 505 continue to operate during "dark" measurements).

Figure 11:
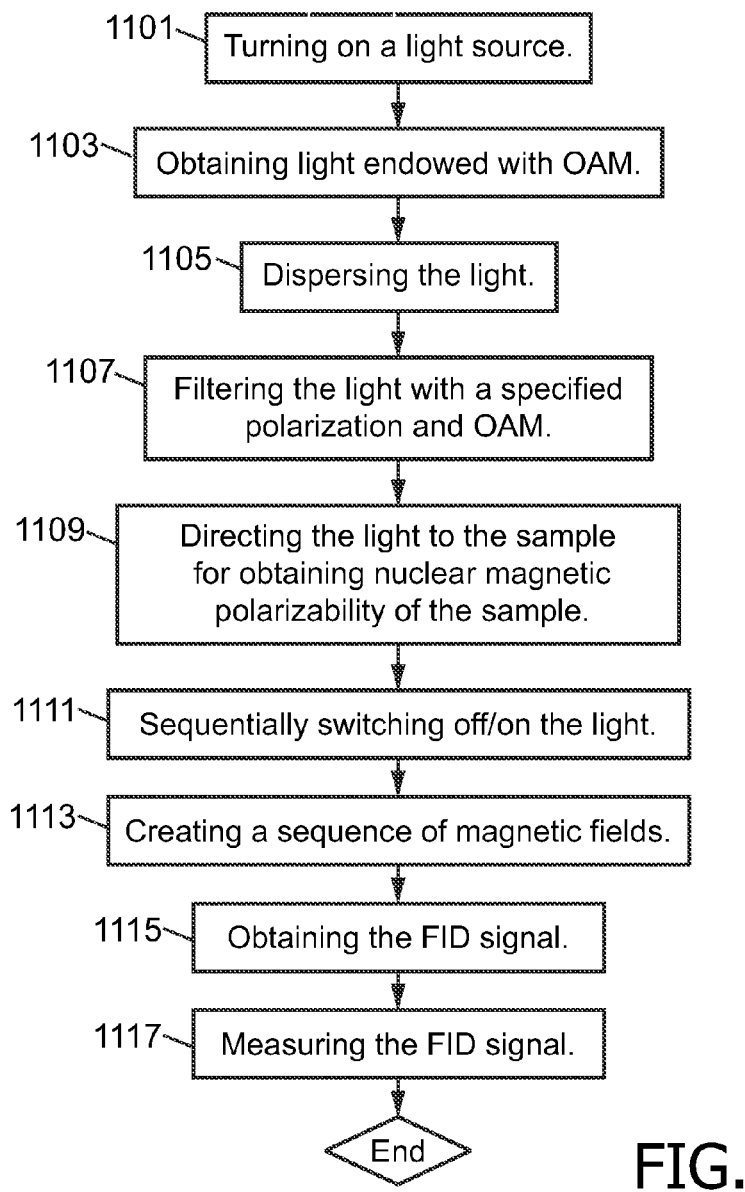
FIG. 11 is a flow chart depicting a method of performing a high resolution fluid analysis in accordance with an embodiment of the present invention.

One embodiment of a method of performing a high resolution fluid analysis is described next with reference to the flow chart of FIG. 11. First in step 1101 the light source 501 is turned on. Then in step 1103 the light acquires OAM and possibly spin once it passes through the polarizer 509, quarter wave plate 511 and SLM apparatus 513.

Then in step 1105 the light is dispersed and in step 1107 the light is filtered with a specified polarization and OAM. It is to be noted that step 1105 is only needed, if OAM is generated by methods that have as a second order effect the light dispersion. Dispersion occurs only when the OAM is generated with diffracting gratings. If the dispersion is generated then it needs to be further filtered for obtaining the first order diffracted beam. In this case the dispersion is done by the SLM unit 513. The filtering is done by using the aperture 517.

Then in step 1109, the light beam is focused onto the sample by using the concave mirror 519 and microscope objective 521. When the light with OAM is applied to the sample, molecule orbitals (electron spins), angular momenta and nuclei will get oriented (Larmor precession movement) around the light beam propagation axis. This process shall produce a detectable FID signal, which shall reflect in peaks in the FID spectrum for the positive edge triggered acquisition, positive edge corresponding to the event "light start passing through the sample". The coil 525 submerged in the fluid serves as an FID detector. The coil symmetry axis overlaps the beam propagation direction, while the center of the coil 525 is positioned on the virtual focal point of the objective.

In step 1111 the light is sequentially switched on and off for obtaining (step 1115) the FID signal. To have a more controlled FID signal, in step 1113 a sequence of magnetic fields is created by the coils 526. These magnetic fields are perpendicular to the direction of the light. When the light is turned off, the magnetic field is created and the thermal nuclei shall relax their orientation, and will get oriented to be more or less aligned with the magnetic field. Thus, the nuclei get oriented into two directions, the first direction being determined by the direction of the light and the second direction being determined by the direction of the magnetic field. In this example the pulse period is about 70 ms and the duty factor is 50%. The applied magnetic field can be a static field or it can be an RF field that is tuned to interact more strongly with specific nuclei. Alternatively this can be done by applying another light beam perpendicular to the first beam. Finally, in step 1117 the obtained FID signal is measured by the measurement coils 523. When light with no OAM (l=0), or when no light is used, no FID signal shall be detected, and thus only noise can be recorded.

More evolved experimental setups require perpendicular coils for different NMR FID excitation sequences, a more efficient method to produce white light and means to modify the light spectrum that is sent to the sample, a more efficient way to modulate the OAM and a better data acquisition (longer acquisition sequences, higher data rates at higher sensitivities) system.

Figure 12:
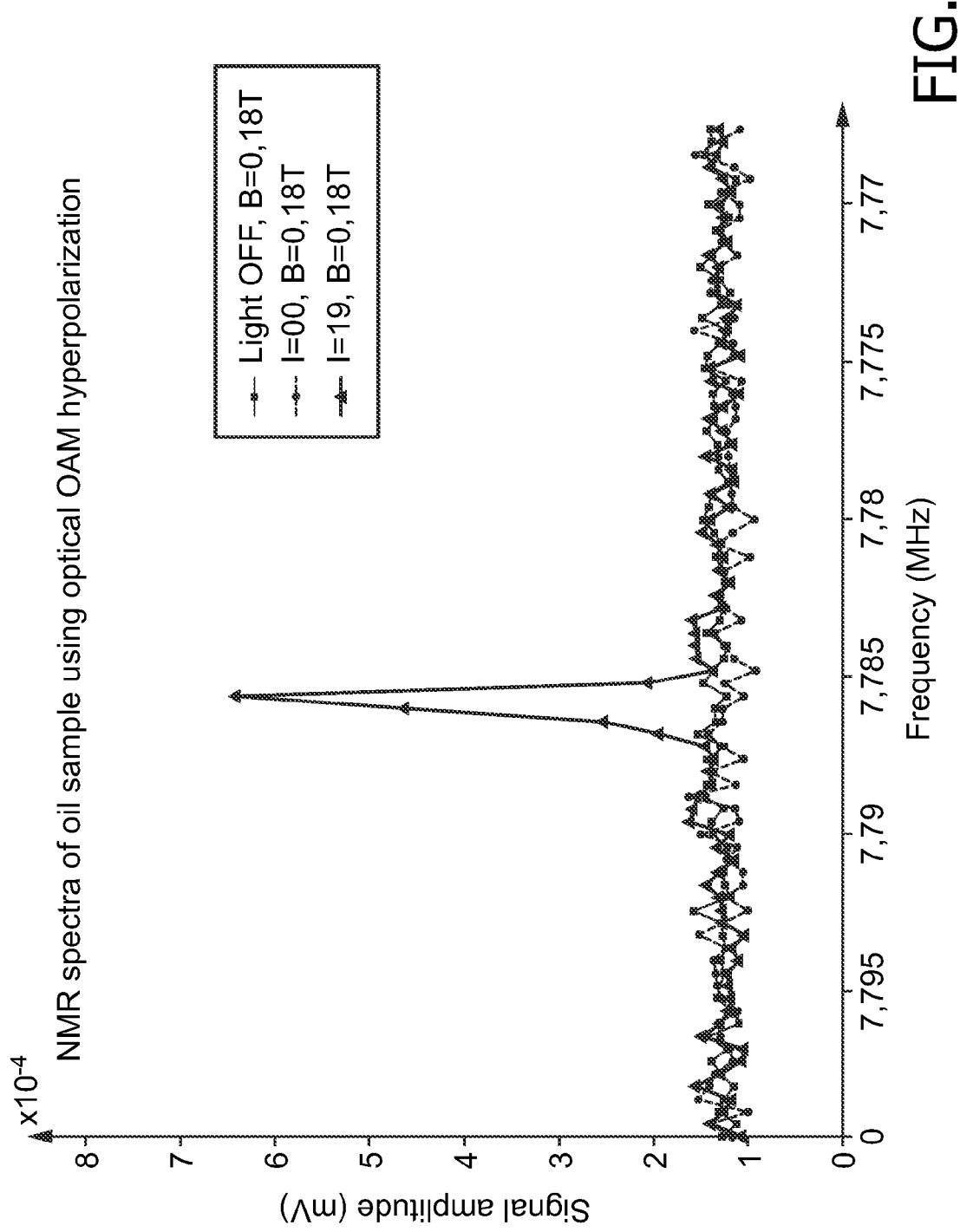
FIG. 12 shows a spectrum of a free induction decay signal.

But even with the modest means of the experimental setup, it was possible to obtain results proving the validity of the concept. FIG. 12 shows a portion of the spectrum obtained from the FID with the acquisition triggered by the negative light edge as shown in FIG. 10 after having carried out the frequency domain transformation by the FFT unit 531. The figure includes the spectrums generated by the sample when it is not irradiated by any light (solid line with rectangles), when it is irradiated by light with no OAM (dotted line with circles), and when it is irradiated by light with OAM (l=19, solid line with triangles). As described above, all of these FIDs were collected in the presence of a perpendicular magnetic B field equal to approximately 0.1 Tesla. The portion of the spectrum depicted in the figure centers on 7.785 MHz, which is approximately where one would expect to see the NMR signature of Hydrogen protons at 0.1 Tesla. No peaks are generated in the absence of light, or with light of l=0. The spectrum is useful, since certain types of atoms and molecules are characterized by a specific distribution of frequency peaks. It is to be noted that the frequency of the light and the OAM carried out by the light affect the position of the peaks.

It can be concluded that the light carrying OAM and spin could produce the orientation of nuclei within a fluid state, therefore the NMR FID can be monitored with NMR signal analysis techniques, without the need of producing high magnetic fields for sample nuclear magnetic momentum polarization.

Figure 13:
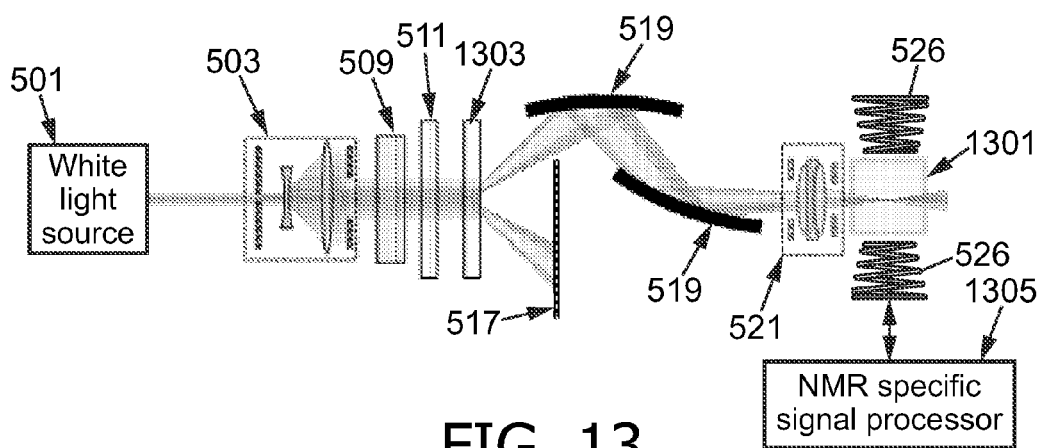
FIG. 13 is a block diagram of another setup for carrying out the sample analysis in accordance with another embodiment of the present invention.

FIG. 13 shows a slightly modified configuration of the configuration of FIG. 5. The apparatus shown in FIG. 13 is equally arranged for performing a high resolution sample analysis based on NMR spectroscopy. Compared to the configuration shown in FIG. 5, in FIG. 13 there is no screen 515 and the SLM 513 is replaced with a holographic plate 1303 for producing the desired type of light endowed with spin and OAM. The LNA 527, photo detector 529, FFT transformation unit 531, controller 533 and driver board 535 are not shown in FIG. 11, but their functioning is integrated into the NMR specific signal processor 1305.

Above some embodiments were described. The invention is applicable in all situations where an NMR chemical sample analysis is required. In particular, it can be used for "in-vivo" applications, e.g. in ePills, intelligent catheters, etc. The embodiments of the invention do not contain any magnetic materials for obtaining hyperpolarized fluid; therefore it is suitable for "in-vivo" operations.

The invention equally relates to a computer program product that is able to implement any of the method steps of the embodiments of the invention when loaded and run on computer means of the devices mentioned above. A computer program may be stored/distributed on a suitable medium supplied together with or as a part of other hardware, but may also be distributed in other forms, such as via the Internet or other wired or wireless telecommunication systems.

The present invention equally relates to an integrated circuit that is arranged to perform any of the method steps in accordance with the embodiments of the invention.

While the invention has been illustrated and described in detail in the drawings and foregoing description, such illustration and description are to be considered illustrative or exemplary and not restrictive; the invention is not restricted to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that different features are recited in mutually different dependent claims does not indicate that a combination of these features cannot be advantageously used. Any reference signs in the claims should not be construed as limiting the scope of the invention.

The invention claimed is:

1. A method of analyzing a sample including molecules based upon nuclear magnetic resonance spectroscopy, the method comprising the acts of:
   providing a light by turning on a light source;
   introducing orbital angular momentum into the light;
   obtaining a focused light beam carrying the orbital angular momentum;
   sequentially illuminating the sample to provide a light pulse for sequential illumination of the sample with the focused light beam carrying the orbital angular momentum for obtaining nuclear magnetic polarization of the sample for aligning the molecules in a propagation direction of the focused light beam when the sample is illuminated by the focused light beam;
   generating a sequence of magnetic fields by a coil arranged around the sample including a magnetic field having a direction which is perpendicular to the propagation direction of the focused light beam, wherein the coil is configured to generate the magnetic field when the sample is not illuminated by the focused light beam for aligning the molecules in the direction of the magnetic field; and
   obtaining a free induction decay signal resulting from the sequential illumination of the sample, the free induction decay signal carrying characteristics of the sample.

2. The method according to claim 1, wherein the focused light beam is further endowed with angular momentum.

3. The method according to claim 1, further comprising the act of stopping the sequential illumination, wherein the act of obtaining the free induction decay signal is perform after the stopping act.

4. The method according to claim 1, wherein the act of obtaining the focused light beam comprises the acts of:
   dispersing the light pulse;
   filtering the dispersed light pulse for obtaining a diffracted beam; and
   directing the diffracted beam by use of a mirror.

5. The method according to claim 1, further comprising the act of comparing the free induction decay signal corresponding to the illuminated sample with another free induction signal corresponding to a non-illuminated sample which is not illuminated with the focused light beam.

6. The method according to claim 1, wherein the nuclear magnetic polarizability of the sample is achieved by the molecules absorbing photons carried by the light thereby transferring to the molecules the orbital angular momentum of the light.

7. The method according to claim 6, wherein as a consequence of the absorption, electron states of the molecules reach a saturated spin state, angular momentum of the molecules is increased and oriented along the propagation direction of the focused light beam, and a magnetic magnetons precession movement associated with the molecules is oriented along the propagation direction of the focused light beam.

8. The method according to claim 1, wherein the act of obtaining the free induction decay signal is performed by the coil arranged around the sample.

9. A non-transitory computer readable medium comprising computer instructions which, when executed by a processor, configure the processor to perform the acts of
   providing a light by turning on a light source;
   introducing orbital angular momentum into the light;
   obtaining a focused light beam carrying the orbital angular momentum;
   sequentially illuminating the sample to provide a light pulse for sequential illumination of the sample with the focused light beam carrying the orbital angular momentum for obtaining nuclear magnetic polarization of the sample for aligning the molecules in a propagation direction of the focused light beam when the sample is illuminated by the focused light beam;
   generating a sequence of magnetic fields by a coil arranged around the sample including a magnetic field having a direction which is perpendicular to the propagation direction of the focused light beam, wherein the coil is configured to generate the magnetic field when the sample is not illuminated by the focused light beam for aligning the molecules in the direction of the magnetic field; and
   obtaining a free induction decay signal resulting from the sequential illumination of the sample, the free induction decay signal carrying characteristics of the sample.

10. A device for analyzing a sample including molecules, the analysis being based upon nuclear magnetic resonance spectroscopy, the device comprising:
    a light source configured to provide a light;
    means for introducing orbital angular momentum into the light;

a container for accommodating the sample;

means for obtaining a focused light beam;

means for sequentially illuminating the sample to provide a light pulse for sequential illumination of the sample with the focused light beam carrying the orbital angular momentum for obtaining nuclear magnetic polarization of the sample for aligning the molecules in a propagation direction of the focused light beam when the sample is illuminated by the focused light beam;

a coil arranged around the sample and configured to generate a sequence of magnetic fields including a magnetic field having a direction which is perpendicular to the propagation direction of the focused light beam, wherein the coil is further configured to generate the magnetic field when the sample is not illuminated by the focused light beam for aligning the molecules in the direction of the magnetic field; and means for detecting a free induction decay signal resulting from the illumination, the free induction decay signal carrying characteristics of the sample.

11. The device according to claim 10, further comprising a Fourier transformation unit configured to transform the free induction decay signal into a frequency domain signal.

12. The device according to claim 10, wherein the means for obtaining a focused light beam comprises means for dispersing the light pulse, means for filtering the dispersed light pulse for obtaining a diffracted light beam, and a mirror for directing the diffracted light beam towards the sample.

13. The device according to claim 10, wherein the coil is further configured to obtain the free induction decay signal.

14. The method of claim 1, further comprising the acts of:

measuring by a photo detector a trigger delay between a mechanical shutter that receives the light from the light source and a raise time of the light pulse passing thorough the sample; and using the trigger delay to trigger the obtaining act.

15. The device of claim 10, further comprising a photo detector configured to measure a trigger delay between a mechanical shutter that receives the light from the light source and a raise time of the light pulse passing thorough the sample, wherein the trigger delay triggers the means for detecting to detect the free induction decay signal.

* * * * *